(12) United States Patent
Van Geel-Schutten et al.

(10) Patent No.: US 6,867,026 B2
(45) Date of Patent: Mar. 15, 2005

(54) GLUCOSYLTRANSFERASES

(75) Inventors: Gerritdina Hendrika Van Geel-Schutten, Driebergen-Rijsendberg (NL); Lubbert Dijkhuizen, Zuidlaren (NL); Hakim Rahaoui, Amersfoort (NL); Robert-Jan Leer, veenendaal (NL)

(73) Assignee: Nederlandse Organisatie Voor Toegepast Natuurwetenschappelijk Onderzoek TNO, Delft (NL)

( * ) Notice: Subject to any disclaimer, the term of this patent is extended or adjusted under 35 U.S.C. 154(b) by 0 days.

(21) Appl. No.: 09/995,749

(22) Filed: Nov. 29, 2001

(65) Prior Publication Data

US 2002/0155568 A1 Oct. 24, 2002

Related U.S. Application Data

(63) Continuation-in-part of application No. 09/604,957, filed on Jun. 28, 2000, now Pat. No. 6,486,314.

(30) Foreign Application Priority Data

May 25, 2000 (EP) .............................................. 00201871

(51) Int. Cl.[7] .......................... C12P 21/06; C12N 9/00; C12N 9/10; C12N 1/20; C12N 15/00
(52) U.S. Cl. ............................... 435/193; 435/4; 435/6; 435/15; 435/41; 435/97; 435/101; 435/183; 435/252.3; 435/252.9; 435/302.1; 536/23.2; 536/23.7
(58) Field of Search ........................... 435/4, 6, 15, 41, 435/97, 101, 183, 193, 252–3, 252.9, 320.1, 194; 536/23–2, 23.7

(56) References Cited

FOREIGN PATENT DOCUMENTS

WO WO 96/06173 A1 * 2/1996

OTHER PUBLICATIONS van Geel–Schutten (c) et al. Appl. Microbiol. Biotechnol., 1998, vol. 50:697–703.*

Ausubel et al. (Short Protocols in Molecular Biology, 1997).*

G.H. van Geel–Schutten et al., Exopolysaccharide Production by *Lactobacillus reuteri*, Involving Sucrase Type of Enzymes, *Med. Fac. Landbouww*, Univ. Gent, V. 65, no. 3a, 2000, pp. 197–201.

G.H. Van Geel–Schutten et al., "Biochemical and Structural Characterization of the Glucan and Fructan Exopolysaccharides Synthesized by the *Lactobacillus reuteri* Wild–Type Strain and by Mutant Strains," *Applied and Environmental Microbiology*, V. 65, no. 7, Jul. 1999, pp. 3008–3014.

Vincent Monchois et al., "Cloning and Sequencing of a Gene Coding for a Novel Dextransucrase from *Leuconostoc Mesenteroides* NRRL B–1299 Synthesizing Only α (1–6) and α (1–3) Linkages," *Gene* (Amsterdam), V. 182, no. 1–2, 1996, pp. 23–32.

Christine L. Simpson et al., "*Streptococcus salivarius* ATCC 25975 Possesses at Least Two Genes Coding for Primer–Independent Glucosyltransferases," *Infection and Immunity*, V. 63, no. 2, 1995, pp. 609–621.

* cited by examiner

*Primary Examiner*—Manjunath N-Rao
(74) *Attorney, Agent, or Firm*—Young & Thompson

(57) ABSTRACT

The present invention describes a protein having glucosyltransferase activity. This protein is derived from lactobacilli, which are food-grade microorganisms with the Generally Recognized As Safe (GRAS) status. The protein produces a glucan with a unique structure having 4-linked, 6-linked and 4,6-linked anhydroglucose units or in the presence of suitable acceptors, oligosaccharides. According to the invention lactobacilli capable of producing this glucan using the novel glucosyltransferase can be used as a probiotic or symbiotic.

17 Claims, 12 Drawing Sheets

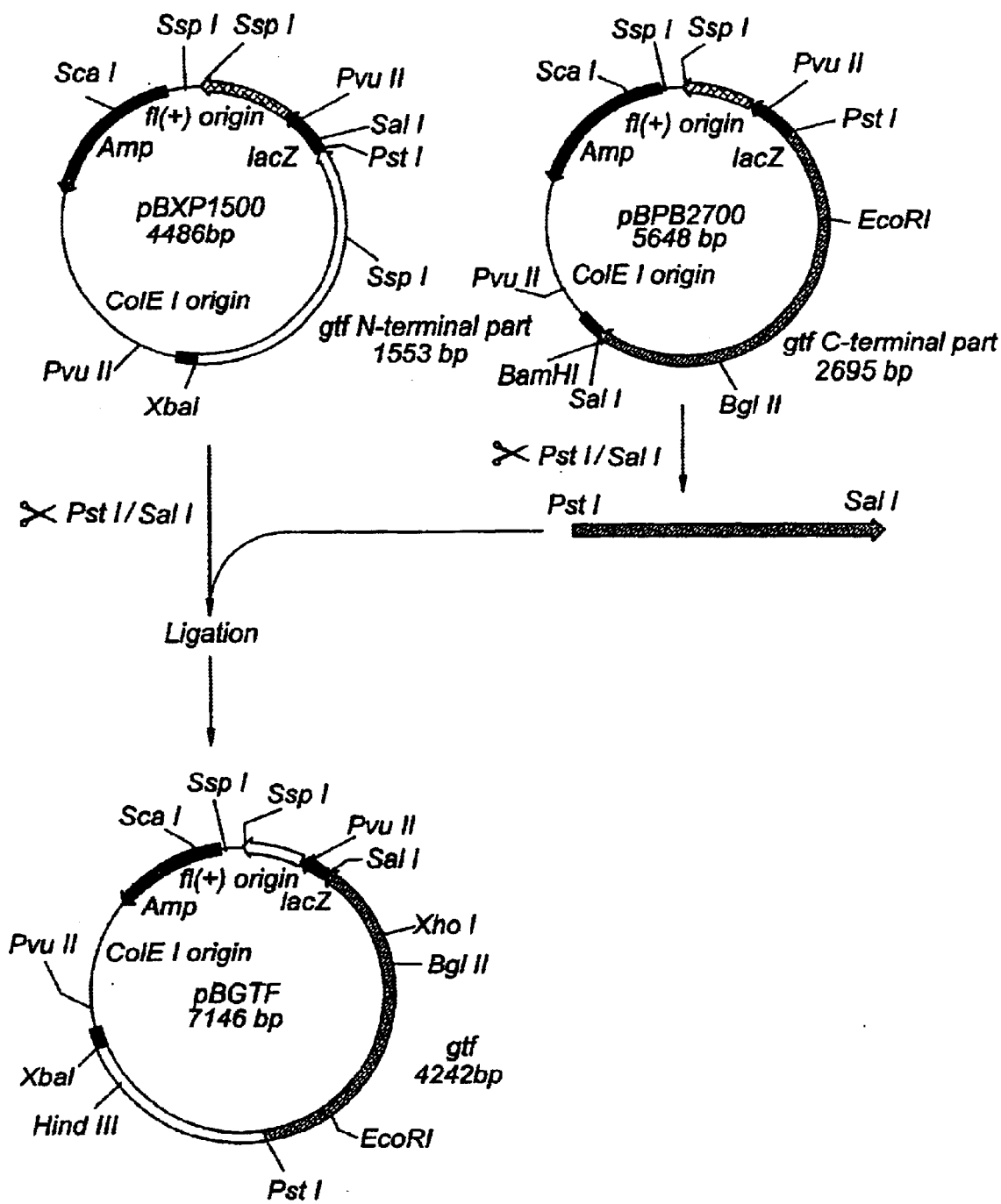

Fig. 3.1

```
                  •                  ◊ ⇓  ▽▽
GTFD    LLANDIDNSNPVVQAEQLNWLHYLMNYGSIVANDPEANFDGVRVDAVDNVNADLLQIASD    480
DSRS    LLANDVDNSNVVVEAEQLNWLYYLMNFGTITANDADANFDGIRVDAVDNVDADLLQIAAD    576
ASR     LLANDIDNSNPIVQAEQLNWLHYLMNFGSITGNNDNANFDGIRVDAVDNVDADLLKIAGD    650
GTFA    LLANDIDNSNPVVQAEQLNWLYYLLNFGTITANNDQANFDSVRVDAPDNIDADLMNIAQD    509
        *****.****.*.*******.**.*.*.*  *    ****.****.**.***.**.*

AS          262QWDLN266                   .290IVRMDAVAFI298
                ------H3------              --E4-    -----H4--

⇓▽▽▽·
GTFD    YLKAHYGVDKSEKNAINHLSILEAWSDNDPQYNKDTKGAQLPIDNKLRLSLLYALTRPLE    540
DSRS    YFKLAYGVDQNDATANQHLSILEDWSHNDPLYVTDQGSNQLTMDDYVHTQLIWSLTK--S    634
ASR     YFKALYGTDKSDANANKHLSILEDWNGKDPQYVNQQGNAQLTMDYTVTSQFGNSLTHGAN    710
GTFA    YFNAAYGMD-SDAVSNKHINILEDWNHADPEYFNKIGNPQLTMDDTIK----NSLNHGLS    564
         *  ** *  ,  , *. *** *  ** *     **.*    .     .*..
        ----        -E5--         ---H5----        ---E6--

GTFD    KDASNKNEIRSGLEPVITNSLN-------------------NRSAEGKNSERMANYIFIRA    582
DSRS    ---SD---IRGTMQRFVDYYMV-------------------DRSNDSTENEAIPNYSFVRA    660
ASR     N-RSN----MWYFLDTGYYLNGDLNKKIVDKNRPNSGTLVNRIANSGDTKVIPNYSFVRA    765
GTFA    D-ATN----RWGLDAIVHQS---------------------LADRENNSTENVVIPNYSFVRA    601
                                                 *    . **.*.**

AS                                                          396FVRS
                 ------------H6------------            --E7--
```

Fig. 3.2

```
         ●⇓
GTFD  HDSEVQTVIAKIIKAQINPKTDGLTFTLDELKQAFKIYNEDM--RQAKKKYTQSNIPTAY    640
DSRS  HDSEVQTVIAQIVSDLYPDVENSLAPTTEQLAAAFKVYNEDE--KLADKKYTQYNMASAY    718
ASR   HDYDAQDPIRKAMIDHGIIKNMQDTFTFDQLAQGMEFYYKDQENPSGFKKYNDYNLPSAY    825
GTFA  HDNNSQDQIQNAIRDVTGKD--YHTFTFEDEQKGIDAYIQDQ-N-STVKKYNLYNIPASY    657
      **   *  *           .      . *.    *  *     ***  *  . .*
AS    HD₄₀₁
                                                              ----H7-

GTFD  ALMLSNKDSITRLYYGDMYSDDGQYMATKSPYYDAIDTLLKARIKYAAGGQDMKITYVEG    700
DSRS  AMLLTNKDTVPRVYYGDLYTDDGQYMATKSPYYDAINTLLKARVQYVAGGQ---------    769
ASR   AMLLTNKDTVPRVYYGDMYLEGGQYMEKGTIYNPVISALLKARIKYVSGGQTMATDSSGK    885
GTFA  AILLTNKDTIPRVYYGDLYTDGGQYMEHQTRYYDTLTNLLKSRVKYVAGGQSMQTMSVG-    716
      *..*.***.. *.****.*  ****   .  *  .  ***.*..* .***
AS           ₄₈₈GLPRIYLGD₄₉₆
       H7-       --E8-            -------H8------

GTFD  DKSHMDWDYTGVLTSVRYGTGANEATDQGSEATK----TQGMAVITSNNPSLKLNQNDKV   756
DSRS  ---SMSVDSNDVLTSVRYGKDAMTASDTGTSETR----TEGIGVVIVSNNAELQLEDGHTV  822
ASR   DL---KDGETDLLTSVRFGKGIMTSDQTTTQDNSQDYKNQGIGVIVGNNPDLKLNNDKTI   942
GTFA  -------GNNNILTSVRYGKGAMTATDTGTDETR----TQGIGVVVSNTPNLKLGVNDKV   765
            .*****.*        .   .   ..*. *. *.  *.*

GTFD  IVNMGAAHKNQEYRPLLLTTKDGLTSYTSDAAAKSLYRKTND---------K-GELVFD    805
DSRS  TLHMGAAHKNQAYRALLSTTADGLAYYDTDENAPVAYTDAN------------GDLIFT    869
ASR   TLHMGKAHKNQLYRALVLSNDSGIDVYDSDDKAPTLRTNDNGDLIFHKTNTFVKQDGTII  1002
GTFA  VLHMGAAHKNQQYRAAVLTTTDGVINYTSDQGAPVAMTDENGDLYLSSHNLVVNGK-EEA   824
      ..** ***** **  ...  *.  * * *            *
```

Fig. 3.3

```
GTFD  ASDIQGYLNPQVSGYLAVWVPVGASDNQDVRVAASNKANATG-QVYESSSALDSQLIYEG   864
DSRS  NESIYGVQNPQVSGYLAVWVPVGAQQDQDDARTASDTTTNTSD-KVFHSNAALDSQVIYEG   928
ASR   NYEMKGSLNALISGYLGVWVPVGASDSQDARTVATESSSSNDGSVFHSNAALDSNVIYEG  1062
GTFA  DTAVQGYANPDVSGYLAVWVPVGASDNQDARTAPSTEKNSGN-SAYRTNAAFDSNVIFEA   883
         . *   *  .**** ******   ** *              . . .* **..*.*
                                                              -E1-

GTFD  FSNFQDFVTKDSDYTNKKIAQNVQLFKSWGVTSFEMAPQYVSSEDG-----SFLDSIIQN   919
DSRS  FSNFQAFATDSSEYTNVVIAQNADQFKQWGVTSFQLAPQYRSSTDT-----SFLDSIIQN   983
ASR   FSNFQAMPTSPEQSTNVVIATKANLFKELGITSFELAPQYRSSGDTNYGGMSFLDSFLNN  1122
GTFA  FSNFVYTPTKESERANVRIAQNADFFASLGFTSFEMAPQYNSSKDR-----TFLDSTIDN   938
      ****   *    .*  ** .     *   * ***.**** ** *      .****  . *
AS                            134GLTYLHLMP142
      ---H1--           --E2-

GTFD  GYAFEDRYDLAMSKN--N----KYGSQQDMINAVKALHKSGIQVIADWVPDQ   965
DSRS  GYAFTDRYDLGYGTP--T----KYGTADQLRDAIKALHASGIQAIADWVPDQ  1029
ASR   GYAFTDRYDLGFNKADGNPNPTKYGTDQDLRNAIEALHKNGMQAIADWVPDQ  1174
GTFA  GYAFTDRYDLGMSEP--N----KYGTDEDLRNAIQALHKAGLQVMADWVPDQ   984
      **** *****          ***.  . *.*** *.* *******
AS                                              190DFITNH195
                                       ------H2------  ---E3--
```

Fig.4.1

```
                       ◊ ⇓  ∇∇
GTFD  LLANDIDNSNPVVQAEQLNWLHYLMNYGSIVANDPEANFDGVRVDAVDNVNADLLQIASD   480
DSRS  LLANDVDNSNVVVEAEQLNWLYYLMNFGTITANDADANFDGIRVDAVDNVDADLLQIAAD   576
ASR   LLANDIDNSNPIVQAEQLNWLHYLMNFGSITGNNDNANFDGIRVDAVDNVDADLLKIAGD   650
GTFA  LLANDIDNSNPVVQAEQLNWLYYLLNFGTITANNDQANFDSVRVDAPDNIDADLMNIAQD   509
      ****.****  .*.******* **.*.* *    ****  .**** **. ***. ** *

AS    262QWDLN266                  .290IVRMDAVAFI298
         ------H3------                --E4-    -----H4--
```

```
                ⇓∇∇∇
GTFD  YLKAHYGVDKSEKNAINHLSILEAWSDNDPQYNKDTKGAQLPIDNKLRLSLLYALTRPLE   540
DSRS  YFKLAYGVDQNDATANQHLSILEDWSHNDPLYVTDQGSNQLTMDDYVHTQLIWSLTK--S   634
ASR   YFKALYGTDKSDANANKHLSILEDWNGKDPQYVNQQGNAQLTMDYTVTSQFGNSLTHGAN   710
GTFA  YFNAAYGMD-SDAVSNKHINILEDWNHADPEYFNKIGNPQLTMDDTIK----NSLNHGLS   564
       *  ** *   .  .  *. *** *  **  *     ** .*  .     .*..
          ----         -E5--          ---H5----       ---E6--
```

```
GTFD  KDASNKNEIRSGLEPVITNSLN-----------------NRSAEGKNSERMANYIFIRA   582
DSRS  ---SD----IRGTMQRFVDYYMV------------------DRSNDSTENEAIPNYSFVRA   660
ASR   N-RSN----MWYFLDTGYYLNGDLNKKIVDKNRPNSGTLVNRIANSGDTKVIPNYSFVRA   765
GTFA  D-ATN----RWGLDAIVHQS-----------------LADRENNSTENVVIPNYSFVRA   601
                                              *     . ** *.**

AS                                                  396FVRS
         ------------H6------------              --E7--
```

```
GTFD  HDSEVQTVIAKIIKAQINPKTDGLTFTLDELKQAFKIYNEDM--RQAKKKYTQSNIPTAY   640
DSRS  HDSEVQTVIAQIVSDLYPDVENSLAPTTEQLAAAFKVYNEDE--KLADKKYTQYNMASAY   718
ASR   HDYDAQDPIRKAMIDHGIIKNMQDTFTFDQLAQGMEFYYKDQENPSGFKKYNDYNLPSAY   825
GTFA  HDNNSQDQIQNAIRDVTGKD--YHTFTFEDEQKGIDAYIQDQ-N-STVKKYNLYNIPASY   657
      **  *  *           .*.         *  *   ***. *. ..*
AS    HD₄₀₁
                                                          ----H7-

GTFD  ALMLSNKDSITRLYYGDMYSDDGQYMATKSPYYDAIDTLLKARIKYAAGGQDMKITYVEG   700
DSRS  AMLLTNKDTVPRVYYGDLYTDDGQYMATKSPYYDAINTLLKARVQYVAGGQ---------  769
ASR   AMLLTNKDTVPRVYYGDMYLEGGQYMEKGTIYNPVISALLKARIKYVSGGQTMATDSSGK   885
GTFA  AILLTNKDTIPRVYYGDLYTDGGQYMEHQTRYYDTLTNLLKSRVKYVAGGQSMQTMSVG-   716
      *..*.***.. *.****.*  **** . *    *  .  ***.*..* .***
AS            ₄₈₈GLPRIYLGD₄₉₆
      H7-        --E8-              --------H8------

GTFD  DKSHMDWDYTGVLTSVRYGTGANEATDQGSEATK----TQGMAVITSNNPSLKLNQNDKV   756
DSRS  ---SMSVDSNDVLTSVRYGKDAMTASDTGTSETR----TEGIGVIVSNNAELQLEDGHTV   822
ASR   DL---KDGETDLLTSVRFGKGIMTSDQTTTQDNSQDYKNQGIGVIVGNNPDLKLNNDKTI   942
GTFA  -------GNNNILTSVRYGKGAMTATDTGTDETR----TQGIGVVVSNTPNLKLGVNDKV   765
       . .*****.*                         ..*. *.  *.  *.*       .

GTFD  IVNMGAAHKNQEYRPLLLTTKDGLTSYTSDAAAKSLYRKTND----------K-GELVFD   805
DSRS  TLHMGAAHKNQAYRALLSTTADGLAYYDTDENAPVAYTDAN------------GDLIFT   869
ASR   TLHMGKAHKNQLYRALVLSNDSGIDVYDSDDKAPTLRTNDNGDLIFHKTNTFVKQDGTII  1002
GTFA  VLHMGAAHKNQQYRAAVLTTTDGVINYTSDQGAPVAMTDENGDLYLSSHNLVVNGK-EEA   824
      .** ***** **  ...    .   * .*    *       *
```

Fig.4.3

```
GTFD  ASDIQGYLNPQVSGYLAVWVPVGASDNQDVRVAASNKANATG-QVYESSSALDSQLIYEG   864
DSRS  NESIYGVQNPQVSGYLAVWVPVGAQQDQDARTASDTTTNTSD-KVFHSNAALDSQVIYEG   928
ASR   NYEMKGSLNALISGYLGVWVPVGASDSQDARTVATESSSSNDGSVFHSNAALDSNVIYEG  1062
GTFA  DTAVQGYANPDVSGYLAVWVPVGASDNQDARTAPSTEKNSGN-SAYRTNAAFDSNVIFEA   883
       .  *   * .****  ******  ** *    .     .. .* **..*.*
                                                         -E1-

GTFD  FSNFQDFVTKDSDYTNKKIAQNVQLFKSWGVTSFEMAPQYVSSEDG-----SFLDSIIQN   919
DSRS  FSNFQAFATDSSEYTNVVIAQNADQFKQWGVTSFQLAPQYRSSTDT-----SFLDSIIQN   983
ASR   FSNFQAMPTSPEQSTNVVIATKANLFKELGITSFELAPQYRSSGDTNYGGMSFLDSFLNN  1122
GTFA  FSNFVYTPTKESERANVRIAQNADFFASLGFTSFEMAPQYNSSKDR-----TFLDSTIDN   938
      ****  .    .  *  ** .  *   * *** .**** ** *      .**** . *
AS                             134GLTYLHLMP142
         ---H1--           --E2-

♦
GTFD  GYAFEDRYDLAMSKN--N----KYGSQQDMINAVKALHKSGIQVIADWVPDQ   965
DSRS  GYAFTDRYDLGYGTP--T----KYGTADQLRDAIKALHASGIQAIADWVPDQ  1029
ASR   GYAFTDRYDLGFNKADGNPNPTKYGTDQDLRNAIEALHKNGMQAIADWVPDQ  1174
GTFA  GYAFTDRYDLGMSEP--N----KYGTDEDLRNAIQALHKAGLQVMADWVPDQ   984
      **** *****      .    ***. . *.*** *.*.*******
AS                                         190DFITNH195
         ------H2------  ---E3--
```

GLUCOSYLTRANSFERASES

CROSS-REFERENCE TO RELATED APPLICATION

This application is a continuation-in-part application of U.S. application Ser. No. 09/604,957 filed on Jun. 28, 2000, now U.S. Pat. No. 6,486,314, Nov. 26, 2002, which claims priority from European Application No. 00201871.1 filed on May 25, 2000.

The present invention is in the field of enzymatic production of biomolecules. The invention is particularly concerned with a novel type of glucosyltransferase derived from lactobacilli and with a process for recombinant production of the enzyme and for the production of useful glucans and gluco-oligosaccharides from sucrose. Furthermore, the invention pertains to the produced glucans and gluco-oligosaccharides.

BACKGROUND OF THE INVENTION

Lactic acid bacteria (LAB) play an important role in the fermentative production of food and feed. Traditionally, these bacteria have been used for the production of for instance wine, beer, bread, cheese and yoghurt, and for the preservation of food and feed, e.g. olives, pickles, sausages, sauerkraut and silage. Because of these traditional applications, lactic acid bacteria are food-grade microorganisms that posses the Generally Recognised As Safe (GRAS) status. Due to the different products which are formed during fermentation with lactic acid bacteria, these bacteria contribute positively to the taste, smell and preservation of the final product. The group of lactic acid bacteria encloses several genera such as *Lactobacillus, Leuconostoc, Pediococcus, Streptococcus*, etc.

In recent years also the health promoting properties of lactic acid bacteria have received much attention. They produce an abundant variety of exopolysaccharides (EPS's). These polysaccharides are thought to contribute to human health by acting as prebiotic substrates, nutraceuticals, cholesterol lowering agents or immunomodulants.

To date high molecular weight polysaccharides produced by plants (such as cellulose, starch and pectin), seaweeds (such as alginate and carrageenan) and bacteria (such as alginate, gellan and xanthan) are used in several industrial applications as viscosifying, stabilising, emulsifying, gelling or water binding agents. Although all these polysaccharides are used as food additives, they originate from organisms not having the GRAS status. Thus they are less desirable than the exopolysaccharides of microorganisms, such as lactic acid bacteria, which have the GRAS status.

The exopolysaccharides produced by lactic acid bacteria can be divided in two groups, heteropolysaccharides and homopolysaccharides; these are synthesized by totally different mechanisms. The former consist of repeating units in which residues of different types of sugars are present and the latter consist of one type of monosaccharide. The synthesis of heteropolysaccharides by lactic acid bacteria, including lactobacilli, has been studied extensively in recent years. Considerable less information is present on the synthesis of homopolysaccharides from lactobacilli, although some studies have been performed. The information on the synthesis of homopolysaccharides in lactobacilli is mainly limited to the synthesis of glucans and only two reports, written by the present inventors, exist on the synthesis of fructans. In one of these reports the *Lactobacillus reuteri* strain LB 121 was found to produce both a glucan and a fructan when grown on sucrose, but only a fructan when grown on raffinose (van Geel-Schutten, G. H. et al., Appl. Microbiol. Biotechnol. (1998) 50, 697–703). In the other report was found that *Lactobacillus reuteri* strain LB 35-5, a spontaneous mutant of *Lactobacillus reuteri* strain LB 121, only produced a glucan when grown on sucrose (van Geel-Schutten, G. H. et al., Appl. Environ. Microbiol. (1999) 65, 3008–3014). In the other report the soluble glucan and fructan were also characterised by their molecular weights (of 3,500 and 150 kDa respectively) and the glucan was reported to be highly branched with a unique structure consisting of a terminal, 4-substituted, 6-substituted, and 4,6-di-substituted α-glucose in a molar ratio 1.1:2.7:1.5:1.0 (van Geel-Schutten, G. H. et al., Appl. Environ. Microbiol. (1999) 65, 3008–3014). No structurally identification of a similar glucan produced by a *Lactobacillus* had been reported before. The fructan was identified as a (2→6)-β-D-fructofuranan (also called a levan). This was the first example of levan synthesis by a *Lactobacillus* species.

SUMMARY OF THE INVENTION

A novel enzyme having glucosyltransferase activity using sucrose as a substrate has now been found in *Lactobacillus reuteri*, and its amino acid sequence and other structural properties have been determined. The enzyme is unique in that it is capable of producing a highly branched glucan with α-1,4- and α-1,6-glucosidic links. The invention thus pertains to an enzyme, to DNA encoding it, to cells containing such DNA and to their use in producing carbohydrates, as defined in the appending claims. The invention also pertains to glucans so produced as well as to oligosaccharides and chemically derivatised glucans.

DESCRIPTION OF THE INVENTION

It was found according to the invention that the glucans are produced by certain *Lactobacillus* strains, in particular by certain strains of *Lactobacillus reuteri*, as a result of the activity of a single glucosyltransferase (glucansucrase).

The nucleotide and amino acid sequence of the novel glucosyltransferase are represented by SEQ ID No. 1 and 2, respectively.

The start codon of the glucosyltransferase is preceded by a putative ribosome binding site with the nucleotide sequence GAAGGAGA (located 5 base pairs upstream of the start codon of the glucosyltransferase; see SEQ ID No. 1). Furthermore, the start codon is preceded by the nucleotide sequence TATAAT, also called Pribnow box or −10 region, (located 42 base pairs upstream of the start codon; see SEQ ID No. 1) and by the nucleotide sequence TTGAAA, also called −35 region (located 80 base pairs upstream of the start codon; see SEQ ID No. 1).

The invention covers a protein having glucosyltransferase activity with sucrose as substrate comprising an amino acid sequence with an amino acid identity of at least 50%, preferably at least 60%, and more preferably at least 70%, compared to the amino acid sequence 531-1781 of SEQ ID No. 2. The invention also covers a part of a protein with at least 15 contiguous amino acids which are identical to the corresponding part of the amino acid sequence 531-1781 of SEQ ID No. 2. The present invention covers a protein having glucosyltransferase activity with sucrose as substrate with an amino acid identity of at least 50%, preferably at least 60%, and more preferably at least 70%, compared to the amino acid sequence of SEQ ID No. 2. The invention also covers a part of a protein with at least 15 contiguous amino acids which are identical to the corresponding part of the amino acid sequence of SEQ ID No. 2. The novel glucosyltransferase has homology with several other proteins as revealed by amino acid sequence alignment. A high homology (FIG. 4) was found with an alternansucrase of *Leuconostoc mesenteroides* strain NRRL B-1355 (46% identity, within 1261 amino acids of amino acid sequence 531-1781 of SEQ ID No. 2) and a dextransucrase of *Leuconostoc mesenteroides* strain NRRL B-512F (44% identity, within 1270 amino acids of amino acid sequence 531-1781 of SEQ ID No. 2). Furthermore, the alignment revealed the presence of various domains also found in the other glucosyltransferases, such as an N-terminal variable domain, a catalytic domain and a C-terminal glucan binding domain. The N-terminal domain shows almost no identity with the N-terminal domains of other glucosyltransferases and an N-terminal signal peptide could not be detected.

The invention also covers a protein comprising an amino acid sequence of at least 100 amino acids, exhibiting at least 55%, preferably at least 65% amino acid identity with the corresponding part of the amino acid sequence 972-1514 (catalytic domain) of SEQ ID No. 2. The catalytic domain shows a high level of homology (about 50% identity) with other known streptococcal and *Leuconostoc* glucosyltransferases and putative functions based on the alignment can be ascribed to several amino acids within this catalytic domain (FIG. 3). Asp-1024, Glu-1061 and Asp-1133 of SEQ ID No. 2 are putative catalytic residues, Asp-984 of SEQ ID No. 2 is a putative calcium binding residue and Arg-1022 of SEQ ID No. 2 a putative chloride binding residue. His-1132 and Gln-1514 of SEQ ID No. 2 may stabilize the transition state and the residues Asp-1027, Asn-1028, Asp-1062 and Trp-1063 of SEQ ID No. 2 may play a role in binding of acceptor molecules and in the transfer of the glucosyl moiety.

The invention further covers a protein comprising an amino acid sequence of at least 100 amino acids, exhibiting at least 50%, preferably at least 60%, amino acid identity with the corresponding part of the amino acid sequence 1515-1781 (glucan binding domain) of SEQ ID No. 2. The C-terminal putative glucan binding domain is much shorter than the corresponding domains in other glucosyltransferases but three known repeats, resembling YG repeats, are described: YYFYDLAGNMVKN (SEQ ID No. 3) starting at amino acid position 1656 of SEQ ID No. 2, WYFFDQDGKMVEN (SEQ ID No. 4) starting at amino acid position 1678 of SEQ ID No. 2 and TYYFDNYGK-MVRN (SEQ ID No. 5) starting at amino acid position 1725 of SEQ ID No. 2. YG repeats are defined by the presence of one or more aromatic residues (of which one is usually tyrosine), followed by 3-4 glycine residues downstream, a hydrophobic residue, a neutral polar residue (usually glycine or asparagine) and 1-3 hydrophobic residues. It is striking that the number of repeats necessary to ensure glucan binding properties is different for enzymes producing a soluble or an insoluble glucan. Possibly the glucan binding domain is also involved in the determination of the glucan structure and the polymer chain growth. Furthermore, this domain seems also necessary for the complete glucosyltransferase activity.

Specific amino acids of the glucosyltransferase that are believed to be important for the unique properties of the enzyme include Pro-1026, Ile-1029, Met-1034, Asn-1035, Ser-1136, Ala-1143, Ile-1170, Leu-1223, Ala-1413, Val-1418, Ala-1428, Leu-1442 of the amino acid sequence of SEQ ID No. 2. So a protein, mutant or part thereof, comprising at least one of the above mentioned amino acids is also part of the invention. Particularly Pro-1026 and Ile-1029 are of interest. Pro-1026 is found in a position where a conserved Val is found in other glucosyltransferases. Compared with Val, the presence of Pro results in a more rigid protein structure. This change of protein structure might influence the glucosidic bonds formed and might explain the unique structure of the glucan. Ile-1029 is also found in a position where a conserved Val is present in other LAB glucosyltransferases not producing α(1,4) bonds. An identical amino acid substitution is observed in amylosucrase, a glucosyltransferase synthesizing α(1,4) bonds.

A nucleotide sequence encoding any of the above mentioned proteins, mutants, variants or parts thereof is also a subject of the invention. Furthermore, the nucleic acid sequences corresponding to expression-regulating regions (promoters, enhancers, terminators) contained in the nucleic acid sequence (1)–(160) or (5507)–(6026) of SEQ ID No. 1 can be used for homologous or heterologous expression of genes. Such expression-regulating sequences are operationally linked to a polypeptide-encoding nucleic acid sequence such as the genes of the glucosyltransferase according to the invention. Inverted repeats are located 62 base pairs downstream the termination codon (TAA), suggesting the presence of a Rho independent transcription termination signal. The −10 and −35 consensus promoter sequences, two motifs generally present upstream of the start codon of procaryotes, are identified as described above. Other promoter, enhancer or terminator were not identified. A nucleic acid construct comprising the nucleotide sequence operationally linked to an expression-regulating nucleic acid sequence is also covered by the invention.

A recombinant host cell, such as a mammalian (with the exception of human), plant, animal, fungal or bacterial cell, containing one or more copies of the nucleic acid construct mentioned above is an additional subject of the invention. The glucosyltransferase gene has been cloned and expressed in *E. coli*. The molecular weight predicted from the first deduced amino acid sequence (i.e. the amino acid sequence 531-1781 of SEQ ID No. 2; see examples) of the recombinant glucansucrase expressed in *E. coli* is 145 kDa.

The invention further covers a enzymatically active protein as defined above which, in the presence of sucrose, produces a glucan having 38–48% 4-linked anhydroglucose units, 17–28% 6-linked anhydroglucose units, and 7–20% 4,6-linked anhydroglucose units, preferably a glucan having 40–46% 4-linked anhydroglucose units, 19–26% 6-linked anhydroglucose units, and 9–18% 4,6-linked anhydroglucose units. There is a large variation in glucans due to differences in the type of bonds present, degree and type of branching, length of the glucan chains, molecular weight, and the conformation of the polymers. The structure of this glucan is unique in that it is highly branched, consists of terminal, 4-substituted, 6-substituted, and 4,6-di-substituted α-glucose in a molar ratio 1.1:2.7:1.5:1.0 and has a high molecular weight of 3500 kDa. The novel glucan may be synthesized by a glucosyltransferase present in the *Lactobacillus* strains, preferably *Lactobacillus reuteri* strains and more preferably *Lactobacillus reuteri* strains LB 121 and LB 35-5. *Lactobacillus reuteri* belongs to the group of lactic acid bacteria which are known to play an important role in the fermentative production of food and feed. Because of this, lactic acid bacteria are food-grade micro-organisms that posses the Generally Recognised As Safe (GRAS) status.

The invention also pertains to a process of producing a glucan as described above. This glucan can be produced by a *Lactobacillus* strain, preferably a *Lactobacillus reuteri* strain, and more preferably *Lactobacillus* strain LB 121 or LB 35-5 or by a recombinant micro-organism expressing the glucosyltransferase according ot the invention or by an isolated glucosyltransferase according to the invention and a suitable glucose source such as for instance sucrose. The glucosyltransferase may be isolated by conventional means from the culture of a glucosyltransferase-positive lactic acid bacterium, especially a *Lactobacillus reuteri*, or from a recombinant organism expressing the glucosyltransferase gene.

Additionally, the invention concerns a process of producing gluco-oligosaccharides containing the characteristic structure of the glucan described above using an isolated glucosyltransferase according to the invention or a *Lactobacillus* strain, preferably a *Lactobacillus reuteri* strain, or a recombinant micro-organism containing a glucosyltransferase according to the invention. There is a growing interest in oligosaccharides derived from homopolysaccharides, for instance for prebiotic purposes. Several fructo- and gluco-oligosaccharides are known to stimulate the growth of bifidobacteria in the human colon. Gluco-oligosaccharides produced by the glucosyltransferase described above can be used as prebiotics and probiotics and are also part of the invention. The production of the gluco-oligosaccharides is different from the glucan synthesis reaction. In addition to sucrose, the substrate of the glucosyltransferase, an acceptor molecule such as maltose or lactose is necessary for the acceptor reaction. Another way of producing gluco-oligosaccharides is by hydrolysis of the glucan described above. This hydrolysis can be performed by known hydrolysis methods such as enzymatic hydrolysis with enzymes such as amylase, dextranase or pullulanase or by acid hydrolysis. The produced gluco-oligosaccharides must contain at least one 1,6- or one 4,6-glucosidic link to be used as prebiotics.

The invention also covers a glucan having 38–48% 4-linked anhydroglucose units, 17–28% 6-linked anhydroglucose units, and 7–20% 4,6-linked (branching) anhydroglucose units, preferably a glucan having 40–46% 4-linked anhydroglucose units, 19–26% 6-linked anhydroglucose units, and 9–18% 4,6-linked anhydroglucose units and a gluco-oligosaccharide containing at least two 4-linked anhydroglucose units, at least one 6-linked anhydroglucose units and at least one 4,6-double linked anhydroglucose units. The novel gluco-oligosaccharides contain at least 5, preferably at least 6 or even at least 8 anhydroglucose units. In addition, they may contain one non-glucose terminal unit such as galactose, mannose or fructose. The glucan and the gluco-oligosaccharides described above can be recovered from the culture supernatant of *Lactobacillus* strains, preferably *Lactobacillus reuteri* strains, and more preferably *Lactobacillus reuteri* strains LB 121 and LB 35-5, containing the glucosyltransferase according to the invention. The glucan can comprise at least 20, up to about 100,000 α-anhydroglucose units with the unique structure described above. The molecular mass of the glucan synthesized by the *Lactobacillus* strains LB 121 and LB 35-5 was 3,500 kDa.

The invention also concerns chemically modified glucans and gluco-oligosaccharides based on the 1,4/1,6-α-glucans described above. Chemical modification can be achieved by oxidation, such as hypochlorite oxidation resulting in ring-opened 2,3-dicarboxy-anhydroglucose units (see e.g. EP-A-427349), periodate oxidation resulting in ring-opened 2,3-dialdehyde-anhydroglucose units (see e.g. WO 95/12619), which can be further oxidised to (partly) carboxylated units (see e.g. WO 00/26257), TEMPO-mediated oxidation resulting in 6-carboxy-anhydroglucose units (see e.g. WO 95/07303). The oxidised glucans have improved water-solubility, altered viscosity and a retarded fermentability and can be used as metal-complexing agents, detergent additives, strengthening additives, bioactive carbohydrates, emulsifiers and water binding agents. They can also be used as starting materials for further derivatisation such as cross-linking and the introduction of hydrophobes. Oxidised glucans coupled to proteins can be used as emulsifiers and stabilizers. (Partial) hydrolysis of glucans according to the invention and/or modified glucans results in gluco-oligosaccharides, which can be used as bioactive carbohydrates or prebiotics. The oxidised glucans of the invention preferably contain 0.05–1.0 carboxyl groups per anhydroglucose unit, e.g as 6-carboxyl units.

Another type of chemical modification is phosphorylation, as described in O. B. Wurzburg (1986) Modified Starches: properties and uses. CRC Press Inc., Boca Raton, 97–112. One way to achieve this modification is by dry heating glucans with a mixture of monosodium and disodium hydrogen phosphate or with tripolyphosphate. The phosphorylated glucans are suitable as wet-end additives in papermaking, as binders in paper coating compositions, as warp sizing-agents, and as core binders for sand molds for metal casting. A further type of derivatisation of the glucans is acylation, especially acetylation using acetic or propionic anhydride, resulting in products suitable as bleaching assistants and for the use in foils. Acylation with e.g. alkenyl succinic anhydrides or (activated) fatty acids results in surface-active products suitable as e.g. surfactants, emulsifiers, and stabilizers.

Hydroxyalkylation, carboxymethylation, and amino-alkylation are other methods of chemical derivatisation of the glucans. Hydroxyalkylation is commonly performed by base-catalysed reaction with alkylene oxides, such as ethylene oxide, propylene oxide or epichlorohydrine; the hydroxyalkylated products have improved solubility and viscosity characteristics. Carboxymethylation is achieved by reaction of the glucans with monochloroacetic acid or its alkali metal salts and results in anionic polymers suitable for various purposes including crystallisation inhibitors, and metal complexants. Amino-alkylation can be achieved by reaction of the glucans with alkylene-imines, halo-alkyl amines or amino-alkylene oxides, or by reaction of epichlorohydrine adducts of the glucans with suitable amines. These products can be used as cationic polymers in a variety of applications, especially as a wet-end additive in paper making to increase strength, for filler and fines retention, and to improve the drainage rate of paper pulp. Other potential applications include textile sizing and wastewater purification. The above mentioned modifications can be used either separately or in combination depending on the desired product. Furthermore, the degree of chemical modification is variable and depends on the intended use. If necessary 100% modification, i.e. modification of all anhydroglucose units can be performed. However, partial modification, e.g. from 1 modified anhydroglucose unit per 100 up to higher levels, will often be sufficient in order to obtain the desired effect.

Use of a *Lactobacillus* strain capable of producing the novel and unique glucan is also covered by the invention. Preferably, the strain is also capable of producing a fructan, which can be either a levan, inulin or both. More preferably, the strain is also capable of producing fructo-oligosaccharides. For producing a glucan and/or fructan mentioned above a *Lactobacillus* strain according to the present invention uses preferably sucrose as a substrate. The glucan according to the invention can be produced when the *Lactobacillus* strain is cultured in the presence of sucrose and/or after the *Lactobacillus* strain was cultured in the presence of sucrose during a sufficient time period. The *Lactobacillus* strains according to the invention are deposited at the BCCM/LMG Culture Collection (Gent, Belgium) under the deposit numbers LMG P-18388 (*Lactobacillus reuteri* wild-type strain LB 121) and LMG P-18389 (*Lactobacillus reuteri* mutant strain LB 35-5). The efficacy of some *Lactobacillus reuteri* strains as a probiotic has been demonstrated in various animals such as for instance poultry and humans. The administration of *Lactobacillus reuteri* to pigs resulted in significantly lower serum total and LDL-cholesterol levels, while in children *Lactobacillus reuteri* is used as a therapeutic agent against acute diarrhea. For this and other reasons *Lactobacillus reuteri* has already been supplemented to commercially available probiotic products. The mode of action of *Lactobacillus reuteri* as a probiotic is still unclear. Preliminary studies indicated that gut colonization by *Lactobacillus reuteri* may be of importance. According to the invention, it was found that the mode of action of *Lactobacillus reuteri* as a probiotic may reside partly in the ability to produce polysaccharides. *Lactobacillus* strains, preferably *Lactobacillus reuteri* strains, more preferably *Lactobacillus reuteri* strains LB 121, LB 35-5 and other strains capable of producing a glucan having 38–48% 4-linked anhydroglucose units, 17–28% 6-linked anhydroglucose units, and 7–20% 4,6-linked anhydroglucose units, preferably a glucan having 40–46% 4-linked anhydroglucose units, 19–26% 6-linked anhydroglucose units, and 9–18% 4,6-linked anhydroglucose units can thus advantageously be used as a probiotic. They can also, together with these polysaccharides, be used as a symbiotic (instead of the term symbiotic, the term synbiotic can also be used).

In that respect, a further aspect of the invention relates to a probiotic of symbiotic composition containing a *Lactobacillus* strain capable of producing a glucan and/or gluco-oligosaccharide according to the invention. Preferably, said strain also produces a fructan. The probiotic or symbiotic compositions of the invention may be directly ingested with or without a suitable vehicle or used as an additive in conjunction with foods. They can be incorporated into a variety of foods and beverages including, but not limited to, yoghurts, ice creams, cheeses, baked products such as bread, biscuits and cakes, dairy and dairy substitute foods, confectionery products, edible oil compositions, spreads, breakfast cereals, juices and the like.

Another aspect of the invention pertains to a process of improving the microbial status in the mammalian colon comprising administering an effective amount of a *Lactobacillus* strain capable of producing a glucan and/or gluco-oligosaccharide according to the invention and/or a fructan.

Furthermore, a process of improving the microbial status of the mammalian colon comprising administering an effective amount of a glucan or gluco-oligosaccharide according to the invention is also a part of the present invention.

EXAMPLES

Example 1

Isolation of DNA from *Lactobacillus reuteri*. Nucleotide Sequence Analysis of the Glucosyltransferase Gene, Construction of Plasmids for Expression of the Glucosyltransferase Gene in *E. coli* DH5α, Expression of the Glucosyltransferase Gene in *E. coli* DH5α, and Identification of the Novel Glucan Produced by the Recombinant Enzyme General procedures for cloning, DNA manipulations and agarose gel electrophoresis were essentially as described by Sambrook et al. (1989) Molecular cloning: a laboratory manual, 2nd ed. Cold Spring Harbour Laboratory Press, Cold Spring Harbour, New York. Restriction endonuclease digestions and ligations with T4 DNA ligase were performed as recommended by the suppliers. DNA was amplified by PCR techniques using ampliTAQ DNA polymerase (Perkin Elmer). DNA fragments were isolated from agarose gels using the Qiagen extraction kit (Qiagen GMBH), following the instructions of the suppliers. *Lactobacillus reuteri* strains were grown anaerobically at 37° C. in MRS medium (DIFCO) or in MRS-s medium (MRS medium containing 100 g/l sucrose instead of 20 g/l glucose) and *E. coli* strains were grown aerobically at 37° C. in LB medium containing 100 μg/ml ampicillin (when appropriate 40 μg/ml X-gal was added).

For the isolation of chromosomal DNA, *Lactobacillus reuteri* 121 was grown overnight at 37° C. in MRS broth (Difco) supplemented with 40 mM DL-threonine. Cells of 4 ml culture were harvested by centrifugation and resuspended in 10 ml MRS broth supplemented with 40 mM DL-threonine and incubated for 2 h at 37° C. After centrifugation the cells were resuspended in 400 μl protoplast buffer (10 mM sodium maleate, pH 6.1 supplemented with 0.3 M lactose, 10 mM MgCi$_2$, 12% polyethyleneglycol 2000, 0.1 M EDTA, 5 mg/ml lysozyme (47,000 U/mg) and 10 U/ml mutanolysine) and incubated for 1 h at 37° C. After centrifugation (1 min, Eppendorf centrifuge), protoplasts were resuspended in 500 μl 20 mM Tris-HCl, pH 8,0. Subsequently, 100 μl laurylsarcosine and 150 μl 5 M NaCl were added and DNA was extracted. Plasmid DNA of *Lactobacillus reuteri* was isolated using a modification of the methods of Anderson and Mc Kay (1983) Appl. Environ. Microbiol. 46, 549–552 and Burger and Dicks (1994) Biotechnol. Technol. 8, 769–772. Fresh prewarmed (37° C.) MRS broth (10 ml) was inoculated with 200 μl of an overnight culture and incubated for 2.5 h at 37° C. Cells were harvested by centrifugation and washed with 2 ml sterile STE buffer (0.1 M NaCl, 10 mM Tris-HCl, 1 mM EDTA, pH 8). After centrifugation, the pellet was resuspended in 380 μl solution I (0.5 M sucrose, 50 mM Tris-HCl, 1 mM EDTA, pH 8, containing 2 mg/ml lysozyme and 6.6 U mutanolysin). After an incubation of 1.5 h at 37° C., 50 μl of solution II (50 mM Tris-HCl, pH 80, 0,25 M EDTA) and 30 μl of solution III (50 mM Tris-HCL, pH 8, 20 mM EDTA, 20% SDS) were added and the suspension was mixed. Sodiumhydroxide (30 μl of a 3 M solution) was added, followed by 50 μl 2 M Tris-HCl and 72 μl 5 N NaCl. After extraction with equal volumes of phenol and chloroform, the DNA was precipitated with ethanol.

The glucosyltransferase (gtfA) gene was identified by amplification with PCR using degenerated primers (GTFprl, 5'GAYAAKWSNAAKSYNRTNGTNSARGC3' (SEQ ID No. 6) and GTFpr2, 5'GNKCNCANATRATRCCNC-TRNA3' (SEQ ID No. 7); Y=T or C, K=G or T, W=A or T, S=C or G, R=A or G, N=A, C, G, or T) based on conserved amino acid sequences deduced from different glucosyltransferase genes (gtfS of *Streptococcus downei*, gtfC of *S. mutans*, gtfI of *S. downei*, gtfK and gtfM of *S. salivarius* and dsrA of *Leuconostoc mesenteroides*) and *Lactobacillus reuteri* chromosomal DNA as template. An amplification product with the predicted size of about 660 bp was obtained (FIG. 1A). To investigate the possible presence of multiple copies of the glucosyltransferase gene, Southern hybridization was performed. DNA was restricted with endonucleases, separated by agarose gel electrophoresis and transferred to a Hybond nylon membrane. For hybridization, probes were labelled wih [α-$^{32}$P]dCTP using Random Primed DNA labeling kit (Boehringer Mannheim), following the manufacturer's instructions. The Southern hybridization of chromosomal DNA of the *Lactobacillus reuteri* strain 121 with the amplified 660 bp PCR fragment, followed by washing under non-stringent conditions (45° C., 0.5×SSC/0.1 SDS) revealed one hybridizing fragment, suggesting the presence of only a single copy of a glucosyltransferase gene in the *Lactobacillus reuteri* strains. The 660 bp fragment was cloned in *E. coli* JM109 using the pCR2.1 vector. Transformations were performed by electroporation using the BioRad gene pulser apparatus at 2.5 kV, 25 μF and 200 Ω, following the instructions of the manufacturer. The fragment was sequenced by the method of Sanger et al. (1977) Proc. Natl. Acad. Sci. USA 74, 5463–5467, confirming that the correct part of the gtfA gene had been isolated. The 660 bp amplified fragment was used to design primers for inverse PCR. Using inverse PCR techniques a 3 kb fragment of the isolated gtfA gene was generated (FIG. 1B). This 3 kb amplicon was identified by sequencing and probes were designed to isolate the EcoRI/BglII and EcoRI/HindIII fragments from a partial DNA library of *Lactobacillus reuteri* in *E. coli* DH5α (FIG. 1C). Positive clones were selected by colony blot hybridization using Hybond-N filters, following the instructions of the supplier and the cloned fragments were sequenced. Attempts to clone the C-terminal part of the glucansucrase gene in *E. coli* DH5α or JM109 using a partial DNA library strategy with different vectors failed. Therefore, the C-terminal part was isolated by inverse PCR. The remaining fragment, located between the EcoRI/BglII and EcoRI/HindIII fragments, was isolated by PCR techniques (FIG. 1D). The amplicons obtained were sequenced directly. To eliminate errors due to the PCR reaction, these fragments were sequenced for at least 4 times, using different clones per PCR reaction. Both DNA strands of the entire glucosyltransferase gene were sequenced twice. In this way the sequence of a 5.5 kb region of the *Lactobacillus reuteri* chromosomal DNA, containing the gtfA gene and its surroundings, were obtained.

The plasmids for expression of the glucosyltransferase gene in *E. coli* DH5α were constructed as described hereafter. A 4.8 kb fragment, containing the entire glucosyltransferase gene was generated by PCR, using the primers GTFpr3 (5'ACAACCACCA TGGAATTAGG TCGCACTGAT GTAAC3') (SEQ ID No. 8) and GTFpr4 (5'GCCAGCTGGA TCCGTCGACT AGTTTATTTT TGATCAAGCA TCTTACC3') (SEQ ID No. 9). Both primers contained suitable restriction enzyme recognition sites at their 5' ends (NcoI in GTFpr3 and BamHI and SalI in GTFpr4). Cloning of this PCR fragment in different vectors failed. Therefore, the strategy depicted in FIG. 2 was followed. Briefly, the PCR product was restricted with XbaI/PstI and PstI/BamHI (FIG. 1; BamHI site was introduced with GTFpr4). The resulting fragments (1503 bp and 2696 bp, respectively) were cloned separately in pBluescriptIISK+ yielding pBXP1500 and pBPB2700. Ligation of the 2700 bp PstI/SalI fragment isolated from pBPB2700 in pBXP1500, digested with PstI and SalI, yielded pBGTF (7146 bp) in *E. coli* DH5α. Plasmid DNA of *E. coli* was isolated using the alkaline lysis method of Birnboim and Doly (1979) Nucleic. Acid Res. 7, 1513–1523 or with a Qiagen plamid kit following the instructions of the supplier. Cells of *E. coli* DH5α with pBGTF were harvested by centrifugation after 16 h of growth. The pellet was washed with 50 mM sodium acetate buffer pH 5.5 containing 1 mM $CaCl_2$ and 1% (v/v) Tween-80 and the suspension was centrifuged again. Pelleted cells were resuspended in 50 mM sodium acetate buffer pH 5.5 containing 1 mM $CaCl_2$, 1% (v/v) Tween-80 and 7.2 mM β-mercaptoethanol. Cells were broken by sonication. Cell debris and intact cells were removed by centrifugation for 15 min at 4° C. at 14,000 rpm in an Eppendorf centrifuge and the resulting cell free extract was used in the enzyme assays.

The glucosyltransferase activity was determined at 37° C. by monitoring the release of fructose from sucrose or by measuring the amount of clucan produced using *E. coli* cell free extracts or *Lactobacillus reuteri* culture supernatant in reaction buffer (50 mM sodium acetate, 1 mM $CaCl_2$, 1% (v/v) Tween-80, 10 g/l sucrose, pH 8). Sucrose, glucose and fructose were determined using commercially available kits. For determination of the molecular weight of the glucosyltransferase produced by *E. coli* or *Lactobacillus reuteri*, SDS-PAGE was performed according to Laemmli (1970) Nature 227, 680–685. SDS-PAGE gels were stained using the PAS activity staining. Glucans were collected by precipitation with ethanol. $^{1}$H-NMR spectroscopy (FIG. 5) and methylation analysis (table 1) were performed as described by van Geel-Schutten et al. (1999) Appl. Environ. Microbiol. 65, 3008–3014. The molecular weights of the glucans were determined by high performance size exclusion chromotography coupled on-line with a multi angle laser light scattering and a differential refractive index detector. After the first nucleotide sequencing of the obtained DNA two putative start codons leading to either a protein encoded by 3834 nucleotides (starting at nucleotide position 1670 of SEQ ID No. 1) or a protein encoded by 3753 nucleotides (starting at nucleotide position 1751 of SEQ ID No. 1) were identified. Both putative start codons were preceded by a putative ribosome binding site, GCAGG (located 4 base pairs upstream of nucleotide position 1751 of SEQ ID No. 1), respectively. At the beginning it was believed that the above mentioned nucleotide forms encoded two glucosyltransferases. Depending on the potential start codon used, one of these glucosyltransferases comprised 1278 amino acids (starting at amino acid positions 504 of SEQ ID No. 2) (3834 nucleotides) and the other comprised 1251 amino acids (starting at amino acid position 531 of SEQ ID No. 2) (3753 nucleotides). The molecular weight (MW) deduced of the amino acid sequence of these glucosyltransferases was 143 and 140 kDa, respectively. The isoelectric point deduced of the amino acid sequence of these glucosyltranferases was 4.73 (for the higher MW protein) and 4.71 (for the lower MW protein), at pH 7, respectively. Surprisingly, the molecular weight of the purified protein from *Lactobacillus reuteri* indicated by SDS-PAGE was not approximately 140 kDa but 180 kDa. After repeating the nucleotide sequencing, it appeared that the above mentioned nucleotide forms did not represent the complete nucleotide sequence of the glucosyltransferase according to the invention, but were merely a part of the complete nucleotide sequence encoding the protein of the invention. The complete nucleotide sequence of the novel glucosyltransferase is represented in SEQ ID No. 1 and the amino acid sequence of said glucosyltransferase is shown in SEQ ID No. 2. All experiments were performed with both the complete nucleotide or amino acid sequence of the protein (SEQ ID No. 1 and 2, respectively) and the partial nucleotide or amino acid sequence mentioned above. The results of the experiments performed with the complete or partial amino acid sequence and the complete or partial nucleotide sequence mentioned above were identical indicating that the part of the glucosyltransferase represented by said partial nucleotide and amino acid sequences is essental for the functionality of the glucosyltransferase according to the invention.

TABLE 1

Methylation analysis of the glucans produced by
Lactobacillus reuteri strains and E. coli GTFA.

| Type of glucosyl units | Lactobacillus reuteri strain 121 | Lactobacillus reuteri strain 35-5 | E. coli GTFA |
|---|---|---|---|
| Glcp-(1→ | 24% | 25% | 21% |
| →4)-Glcp-(1→ | 42% | 43% | 44% |
| →6)-Glcp-(1→ | 22% | 21% | 24% |
| →4,6)-Glcp-(1→ | 12% | 11% | 11% |

Example 2

Adhesion Experiments with Lactobacillus Strains

The adhesion of Lactobacillus reuteri strains to Caco-2 cell lines was determined as described below. Firstly, a bacterial suspension was prepared as follows. Lactobacillus reuteri strains LB 121, 35-5, K24 and DSM20016 and L. rhamnosus LGG (a well known probiotic strain with good adhering properties) were cultured in MRS broth supplemented with 5 µl/ml of methyl-1,2-[$^3$H]-thymidine at 37° C. for 18–20 h before the adhesion assays. The cultures were harvested by centrifugation, washed with phosphate buffered saline (PBS) and resuspended in PBS or PBS supplemented with 30 g/l sucrose (see Table 2) to a final density of about 2×10$^9$ cfu/ml. Prior to the adhesion assay, the cell suspensions in PBS with 30 g/l sucrose were incubated for 1 hour at 37° C., whereas the cell suspensions in PBS were kept on ice for 1 hour. After incubation at 37° C., the suspensions in PBS with sucrose were centrifuged and the cells were washed with and resuspended in PBS to a final density of about 2×10$^9$ cfu/ml.

TABLE 2

Incubation of the different Lactobacillus strains prior to the adhesion assays.

| Lactobacillus strain | Extra incubation | Polysaccharide produced | Group |
|---|---|---|---|
| reuteri 121 | PBS sucrose, 37° C. for 1 hr | glucan and fructan | As |
| reuteri 35-5 | PBS sucrose, 37° C. for 1 hr | glucan | Bs |
| reuteri K24 | PBS sucrose, 37° C. for 1 hr | none | Cs |
| reuteri 121 | PBS on ice | none | D |
| reuteri DSM20016* | PBS on ice | none | E |
| rhamnosus GG | PBS on ice | none | F |

*Type strain of L. reuteri

Caco-2 cells were cultured as follows. Subcultures of Caco-2 cells (ATCC, code HTB 37, human colon adenocarcinoma), stored as frozen stock cultures in liquid nitrogen were used for the adhesion tests. The Caco-2 cells were grown in culture medium consisting of Dulbecco's modified Eagle medium (DMEM), supplemented with heat-inactivated foetal calf serum (10% v/v), non-essential amino acids (1% v/v), L-glutamine (2 mM) and gentamicin (50 µg/ml). About 2,000,000 cells were seeded in 75 cm$^2$ tissue culture flasks containing culture medium and cultured in a humidified incubator at 37° C. in air containing 5% CO$_2$. Near confluent Caco-2 cell cultures were harvested by trypsinisation and resuspended in culture medium. The number of cells was established using a Büker-Türk counting chamber.

For the following experiments a Caco-2 monolayer transport system was used. Caco-2 cells cultured in a two-compartment transport system are commonly used to study the intestinal, epithelial permeability. In this system the Caco-2 cell differentiates into polarized columnar cells after reaching confluency. The Caco-2 system has been shown to simulate the passive and active transcellular tranport of electrolytes, sugars, amino acids and lipophilic compounds (Hillgren et al. 1995, Dulfer et al., 1996, Duizer et al., 1997). Also, a clear correlation between the in vivo absorption and the permeability across the monolayers of Caco-2 cells has been reported (Artursson and Karlsson, 1990). For the present transport studies, Caco-2 cells were seeded on semi-permeable filter inserts (12 wells Transwell plates, Costar) at ca. 100,000 cells per filter (growth area ±1 cm$^2$ containing 2.5 ml culture medium). The cells on the insert were cultured for 17 to 24 days at 37° C. in a humidified incubator containing 5% CO$_2$ in air. During this culture period the cells have been subjected to an enterocyte-like differentiation. Gentamycin was eliminated from the culture medium two days prior to the adhesion assays.

The adhesion assay was performed as follows. PBS was used as exposure medium. 25 µl of a bacterial suspension (2×10$^9$ cfu/ml) were added to 0.5 ml medium. The apical side of the Caco-2 monolayers was incubated with the bacterial suspensions for 1 hour at 37° C. After incubation, remaining fluid was removed and the cells were washed three times with 1 ml PBS. Subsequently, the Caco-2 monolayers were digested overnight with 1 ml 0.1M NaOH, 1% SDS. The lysate was mixed with 10 ml Hionic Fluor scintillation liquid and the radioactivity was measured by liquid scintillation counting using a LKB/Wallac scintillation counter. As a control, the radioactivity of the bacterial suspensions was measured. For each test group, the percentage of bacteria attached to the monolayers was calculated. All adhesion tests were performed in quadruple. In Table 3 the results of the bacterial adhesion test to Caco-2 cellines are given. From the results can be concluded that the glucans and the fructans contribute to the adherence of Lactobacillus reuteri to Caco-2 cellines. This could indicate that Lactobacillus reuteri strains producing EPS possess improved probiotic characteristics or that Lactobacillus reuteri and its polysaccharides could function as an exellent symbiotic.

TABLE 3

The results of the bacterial adhesion test to Caco-2 cellines.

| Group (see Table 1) | % of bacteria bound to the monolayer |
|---|---|
| As | 6.5 |
| Bs | 5.7 |
| Cs | 1.8 |
| D | 2.3 |
| E | 0.9 |
| F | 1.3 |

Example 3

Oxidation of Glucans

For TEMPO-mediated oxidation, a glucan produced as described above (dry weight 1 g, 6.15 mmol) was resuspended in 100 ml water. Next, 2,2,6,6-tetramethylpiperidine-1-oxyl (TEMPO; 1% by weight compared to the polysaccharide (0.01 g, 0.065 mmol)) was added and resuspended in 20 min. Sodium bromide (0.75 g, 7.3 mmol) was added and the suspension was cooled to 0° C. The reaction can also be performed without bromide. A solution of hypochlorite (6 ml, 15% solution, 12.6 mmol) was adjusted to pH 10.0 with 3M HCl and cooled down to 0° C. This solution was added to the suspension of the polysaccharide and TEMPO. The course of the reaction was followed by monitoring the consumption of sodium hydroxide solution, which is equivalent to the formation of uronic acid. After 30 min, 59,5 ml 0.1M NaOH was consumed. This amount corresponds to the formation of 96% uronic acid. Thereafter, the solution was poured out in 96% ethanol (comprising 70% of the volume of the solution) causing the product to precipitate. The white precipitate was centrifuged, resuspended in ethanol/water (70/30 v/v) and centrifuged again. Next, the precipitate was resuspended in 96% ethanol and centrifuged. The obtained product was dried at reduced pressure. The uronic acid content was determined by means of the uronic acid assay according to Blumenkrantz and Abdoe-Hansen (Anal. Biochem., 54 (1973), 484). A calibration curve was generated using polygalacturonic acid (5, 10, 15 and 20 µg). With this calibration curve the uronic acid content in a sample of 20 µg of the product was determined. The obtained result was a content of 95% uronic acid with a yield of 95%.

For partial oxidation (about 6%), a glucan produced as described before (dry weight 7.5 g, 46.4 mmol) was resuspended in 50 ml water. Next, TEMPO (1% by weight compared to the polysaccharide (0.075 g, 0.5 mmol)) was added, resuspended in 20 min and cooled to 0° C. A solution of hypochlorite (2.8 ml, 15% solution, 5.9 mmol) was adjusted to pH 9.0 with 3M HCl and cooled down to 0° C. This solution was added to the suspension of the polysaccharide and TEMPO. Within 5 min the mixture became a solid gel.

DESCRIPTION OF THE FIGURES

SEQ ID No. 2: The deduced amino acid sequence of glucosyltransferase A (GTFA) of *Lactobacillus reuteri*.

FIG. 2: The general principle of the construction of the recombinant plasmid with the gtfA gene. A PCR product containing the gtfA gene was digested with XbaI and PstI and with PstI and BamHI. The XbaI/PstI (depicted in white) was ligated into the multiple cloning site of pBluescriptIISK+ in the same direction relatively to the lacZ promotor, resulting in pBXP1500. The PstI/BamHI part (depicted in grey) was ligated into the multiple cloning site of pBluescriptIISK+ in the opposite direction relatively to the lacZ promotor, resulting in pBPB2700. pBXP1500 was used as a vector for subcloning the C-terminal part of the gtfA. pBPB2700 was digested with PstI and SalI and ligated into pBXP1500, also digested with PstI and SalI. The resulting plasmid, pBGTF, contained the entire gtfA in the same direction relative to the lacZ promotor. The ⊒ sign indicates the restriction.

FIG. 3: Alignment of catalytic cores of alternansucrase (ASR) of *Leuconostoc mesenteroides* strain NRRL B-1355 dextransucrase (DSRS) of *Leuconostoc mesenteroides* strain NRRL B-512F, glucosyltransferase-D (GTFD) of *Streptococcus mutans* GS5, glucosyltransferase-A of *Lactobacillus reuteri* and amylosucrase (AS) of *Neisseria polysaccharea*. * indicates identical or conserved residues in all sequences); - - - , gap in the sequence; AA amino acids which are conserved in all other glucosyltransferases but not in GTFA; ↓, putative catalytic residues; •, putative calcium binding sites; ♦, putative residues stabilizing the transition state; ▽, residues possibly playing a role in binding of acceptor molecules and in the transfer of the glucosyl residue; ◇, putative chloride binding sites; -Ex-, localization of β-strands; -Hx-, localization of α-helices according to Mac Gregor et al. (1996) FEBS Lett. 378, 262–266. The numbering of the amino acids of the glucosyltransferase-A of *Lactobacillus reuteri* corresponds to the positions of these amino acids in the amino acid sequence 531-1781 of amino acid sequence SEQ ID No. 2, when the amino acid sequence 531-1781 is renumbered 1-1251. In figures 3.1–3.3, GTFD corresponds to SEQ ID NO. 10. DSRS corresponds to SEQ ID No. 11. ASR corresponds to SEQ ID NO. 12. GTFA corresponds to SEQ ID NO. 13. QWDLN$_2$ corresponds to SEQID NO. 14. IURMDAVAFI corresponds to SEQ ID NO. 15. FVRS corresponds to SEQ ID NO. 16. GLPRIYLGD corresponds to SEQ ID NO. 17. GLLTYLHLMP corresponds to SEQ ID NO. 18. DFITNH corresponds to SEQ ID NO. 19.

SEQUENCE LISTING

Figure 1:
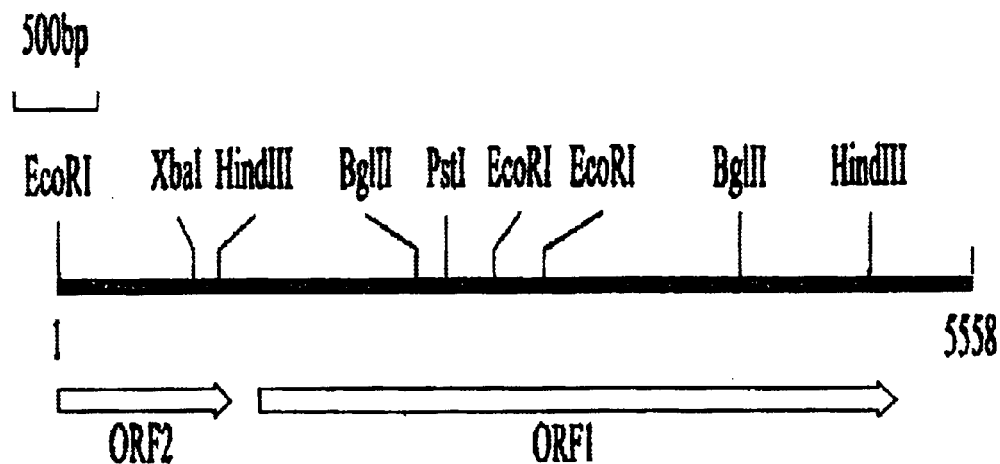
FIG. 1: The strategy used for the isolation of the gtfA gene from *Lactobacillus reuteri* 121 chromosomal DNA.
Figure 4:
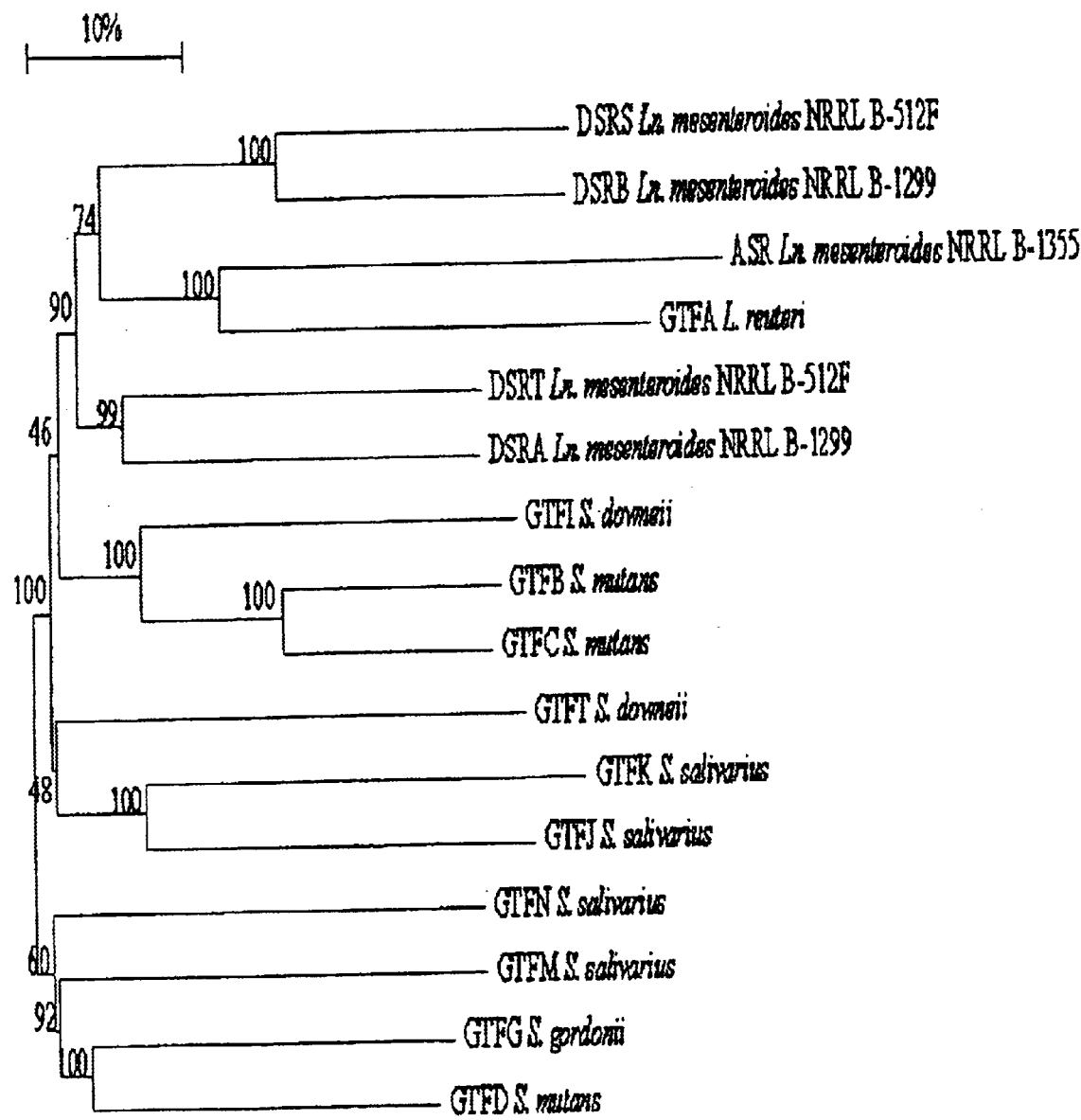
FIG. 4: Dendrogram of glucansucrases of lactic acid bacteria. The horizontal distances are a measure for the difference at the amino acid sequence level. 10% difference is indicated by the upper bar. Bootstrap values (in percentages) are given at the root of each branch.
Figure 5:
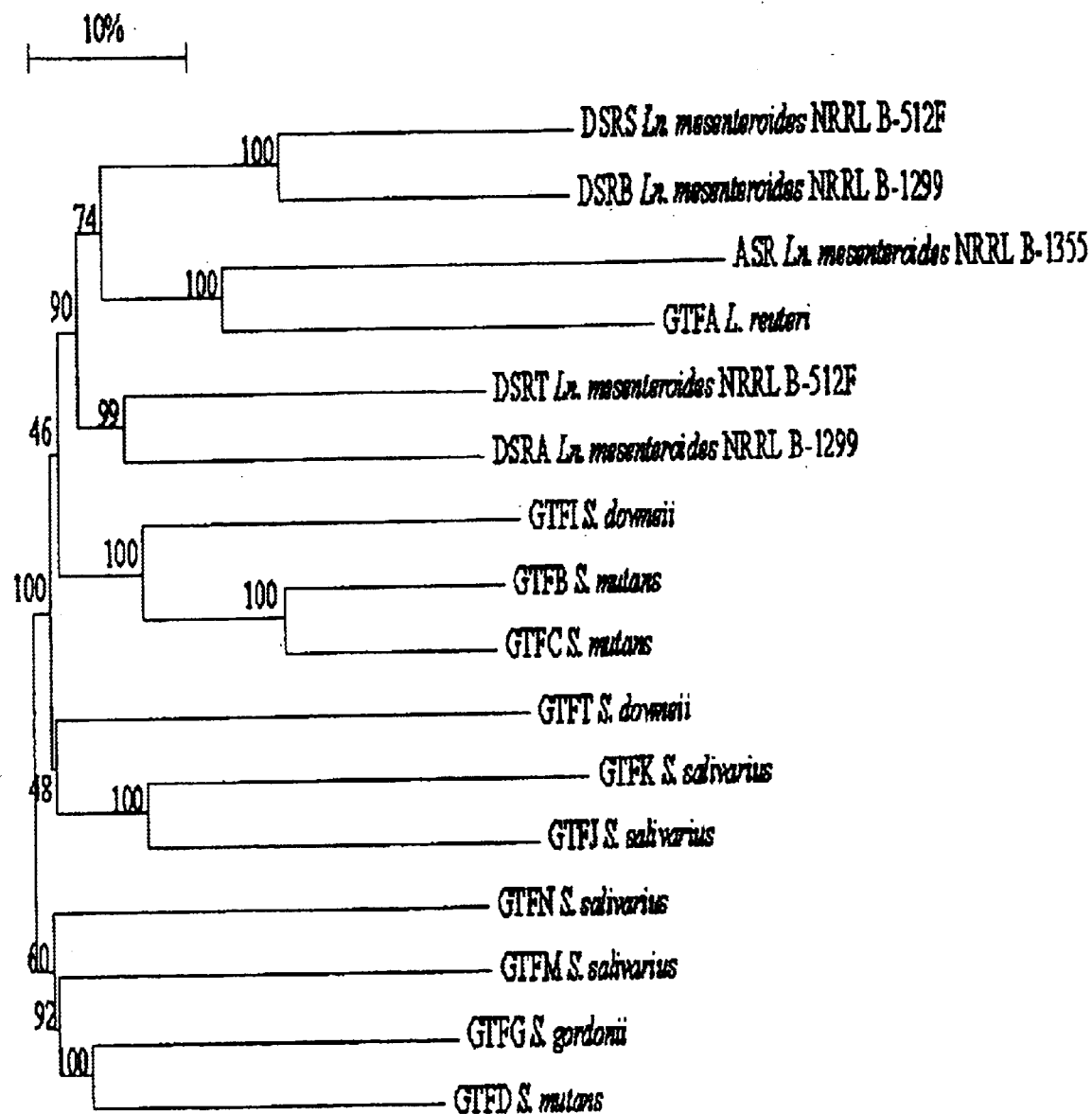
FIG. 5: 500-MHz $^1$H-NMR spectra of the glucan produced by *Lactobacillus reuteri* GTFA (A) and by *E. coli* GTFA (B), recorded in D$_2$O at 80° C.
Figure 5A:
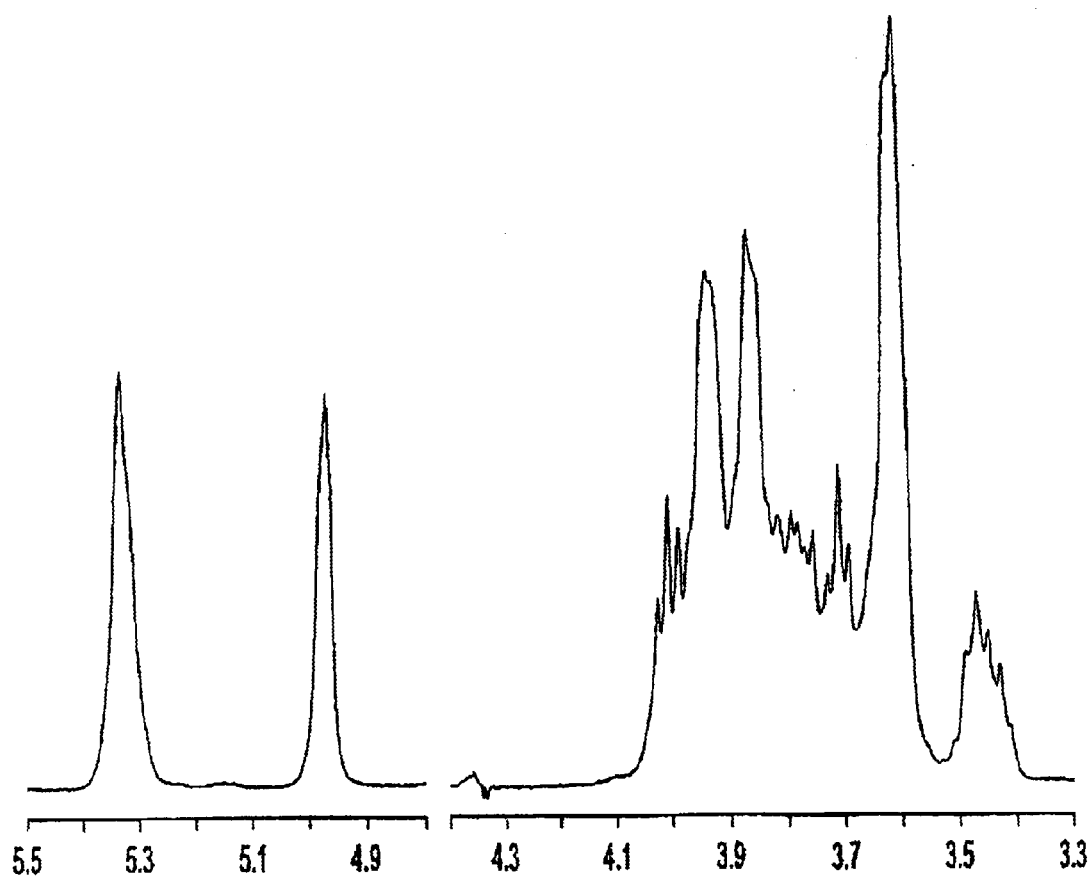
Figure 5B:
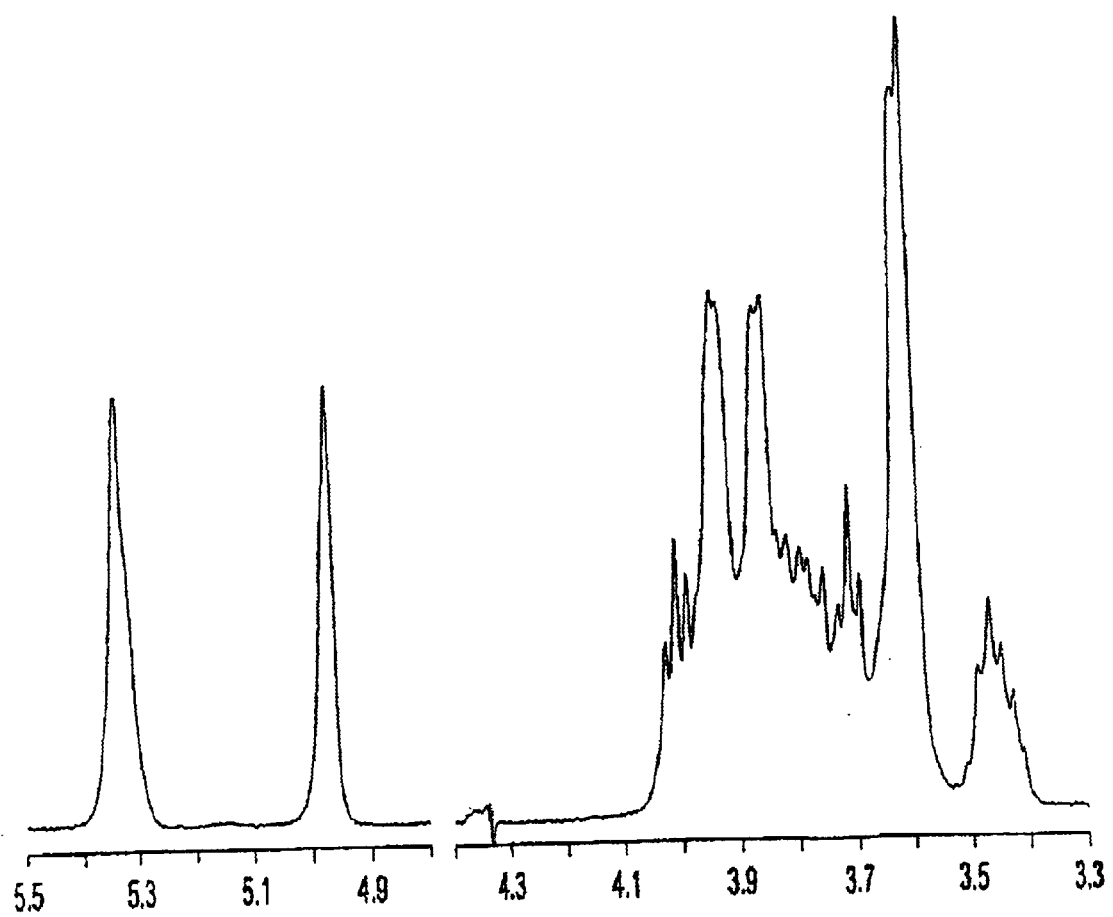

```
<160> NUMBER OF SEQ ID NOS: 19

<210> SEQ ID NO 1
<211> LENGTH: 6026
<212> TYPE: DNA
<213> ORGANISM: Lactobacillus reuteri
<220> FEATURE:
<221> NAME/KEY: CDS
<222> LOCATION: (161)..(5503)

<400> SEQUENCE: 1
atacatattt tgggcttctt tttttgttta aaactgtaaa tttgaatttt atttgaaaaa        60
attttggcta gaatttgaaa attccctttg aaaaaataaa acatcatagt attataatac       120
```

-continued

```
cgataatcaa attgtttatt ttgatatgaa ggagattaaa atg gaa ata aag aaa      175
                                             Met Glu Ile Lys Lys
                                              1               5 cat ttt aag ttg tac aaa agc ggc aaa caa tgg gta aca gca gca gtg      223
His Phe Lys Leu Tyr Lys Ser Gly Lys Gln Trp Val Thr Ala Ala Val
             10                  15                  20 gct acc gtt gcc gtt tca act gcg ctt ctt tac gga gga gtt gcg cat      271
Ala Thr Val Ala Val Ser Thr Ala Leu Leu Tyr Gly Gly Val Ala His
         25                  30                  35 gct gac caa caa gtt cag caa gct tcc acg act caa gac caa act tct      319
Ala Asp Gln Gln Val Gln Gln Ala Ser Thr Thr Gln Asp Gln Thr Ser
     40                  45                  50 acc gta aat aat gat act gat aaa aca gta gct tta gat act aat act      367
Thr Val Asn Asn Asp Thr Asp Lys Thr Val Ala Leu Asp Thr Asn Thr
 55                  60                  65 gac cag tca gct caa aca act gat aaa aaa caa gta gta tca aat act      415
Asp Gln Ser Ala Gln Thr Thr Asp Lys Lys Gln Val Val Ser Asn Thr
 70                  75                  80                  85 aac caa agc aaa act gat gac act tca aca gct gat aag aat tct act      463
Asn Gln Ser Lys Thr Asp Asp Thr Ser Thr Ala Asp Lys Asn Ser Thr
             90                  95                 100 tct aca cct gtt tct gtt ttg cca tct aat aat act gaa aaa caa gct      511
Ser Thr Pro Val Ser Val Leu Pro Ser Asn Asn Thr Glu Lys Gln Ala
            105                 110                 115 aaa aat tat aat gag caa gac aaa gga aac tat ggg aat att gat act      559
Lys Asn Tyr Asn Glu Gln Asp Lys Gly Asn Tyr Gly Asn Ile Asp Thr
        120                 125                 130 gct tac ttt agc aat aat caa ttg cat gtt tca gga tgg aat gca acg      607
Ala Tyr Phe Ser Asn Asn Gln Leu His Val Ser Gly Trp Asn Ala Thr
    135                 140                 145 aac gca tct caa gga aca aac agt cga caa atc att gtg cgt gat atc      655
Asn Ala Ser Gln Gly Thr Asn Ser Arg Gln Ile Ile Val Arg Asp Ile
150                 155                 160                 165 aca acc aat aat gaa tta ggt cgc act gat gta aca aac aat gtt gca      703
Thr Thr Asn Asn Glu Leu Gly Arg Thr Asp Val Thr Asn Asn Val Ala
                170                 175                 180 cgc cca gac gtt aag aat gtt cat aat gtt tat aac gct gat aat tct      751
Arg Pro Asp Val Lys Asn Val His Asn Val Tyr Asn Ala Asp Asn Ser
            185                 190                 195 gga ttt gat gtt aat gtc aat att gac ttt agc aag atg aaa gat tat      799
Gly Phe Asp Val Asn Val Asn Ile Asp Phe Ser Lys Met Lys Asp Tyr
        200                 205                 210 cgg gat tca att gaa att gtt agt cga tac agt gga aac ggt aaa tct      847
Arg Asp Ser Ile Glu Ile Val Ser Arg Tyr Ser Gly Asn Gly Lys Ser
    215                 220                 225 gtt gac tgg tgg tcc caa ccg atc act ttt gac aaa aac aac tat gct      895
Val Asp Trp Trp Ser Gln Pro Ile Thr Phe Asp Lys Asn Asn Tyr Ala
230                 235                 240                 245 tat ctt gat aca ttt gaa gtg aaa aat ggc gaa tta cat gca acc gga      943
Tyr Leu Asp Thr Phe Glu Val Lys Asn Gly Glu Leu His Ala Thr Gly
                250                 255                 260 tgg aat gct act aat agt gcg att aac tat aat cac cat ttt gtg att      991
Trp Asn Ala Thr Asn Ser Ala Ile Asn Tyr Asn His His Phe Val Ile
            265                 270                 275 ttg ttt gat caa acg aat ggt aaa gaa gta gca cga caa gaa gtt cgt     1039
Leu Phe Asp Gln Thr Asn Gly Lys Glu Val Ala Arg Gln Glu Val Arg
        280                 285                 290 gaa ggt caa tca cgc cca gat gtt gct aag gta tat cca caa gta gtt     1087
Glu Gly Gln Ser Arg Pro Asp Val Ala Lys Val Tyr Pro Gln Val Val
    295                 300                 305
```

-continued

| | |
|---|---|
| ggt gct gcc aac tca ggc ttt aat gtg aca ttt aat atc agt gat tta<br>Gly Ala Ala Asn Ser Gly Phe Asn Val Thr Phe Asn Ile Ser Asp Leu<br>310                                  315                        320                       325 | 1135 |
| gat tat act cac cag tac caa gtt ctt agt cgt tac agc aat tct gat<br>Asp Tyr Thr His Gln Tyr Gln Val Leu Ser Arg Tyr Ser Asn Ser Asp<br>                            330                        335                       340 | 1183 |
| aat ggc gaa ggt gat aac gtt acc tac tgg ttt aat cca caa tcc att<br>Asn Gly Glu Gly Asp Asn Val Thr Tyr Trp Phe Asn Pro Gln Ser Ile<br>345                                  350                        355 | 1231 |
| gct cct gct aat caa agt aac cag ggt tat cta gac tca ttt gat att<br>Ala Pro Ala Asn Gln Ser Asn Gln Gly Tyr Leu Asp Ser Phe Asp Ile<br>                     360                        365                       370 | 1279 |
| agt aaa aat ggt gaa gta aca gta act gga tgg aac gct act gac ttg<br>Ser Lys Asn Gly Glu Val Thr Val Thr Gly Trp Asn Ala Thr Asp Leu<br>375                                  380                        385 | 1327 |
| tca gaa tta caa aac aac cat tat gtg att cta ttt gat cag aca gca<br>Ser Glu Leu Gln Asn Asn His Tyr Val Ile Leu Phe Asp Gln Thr Ala<br>390                                  395                        400                       405 | 1375 |
| ggc aaa caa gtt gca tct gct aaa gct gat tta att tca cgt cca gat<br>Gly Lys Gln Val Ala Ser Ala Lys Ala Asp Leu Ile Ser Arg Pro Asp<br>                     410                        415                       420 | 1423 |
| gtt gct aaa gct tat cca aca gta aaa aca gct aca aat tct ggc ttc<br>Val Ala Lys Ala Tyr Pro Thr Val Lys Thr Ala Thr Asn Ser Gly Phe<br>                  425                        430                       435 | 1471 |
| aag gta aca ttt aag gtt aat aac tta caa ccg ggt cac caa tac agc<br>Lys Val Thr Phe Lys Val Asn Asn Leu Gln Pro Gly His Gln Tyr Ser<br>                       440                        445                       450 | 1519 |
| gtt gta agt cgt ttc tct gcc gat gaa aat ggt aat ggt aat gat aag<br>Val Val Ser Arg Phe Ser Ala Asp Glu Asn Gly Asn Gly Asn Asp Lys<br>455                                  460                        465 | 1567 |
| cgc cat aca gat tac tgg ttt agt cca gta ata tta aac cag act gct<br>Arg His Thr Asp Tyr Trp Phe Ser Pro Val Ile Leu Asn Gln Thr Ala<br>470                                  475                        480                       485 | 1615 |
| tca aac att gat act att aca atg aca tct aat ggt tta cat att gca<br>Ser Asn Ile Asp Thr Ile Thr Met Thr Ser Asn Gly Leu His Ile Ala<br>                     490                        495                       500 | 1663 |
| ggt tgg atg gca agt gat aac tca att aat gaa aca act cca tac gct<br>Gly Trp Met Ala Ser Asp Asn Ser Ile Asn Glu Thr Thr Pro Tyr Ala<br>                  505                        510                       515 | 1711 |
| att atc ctc aat aat gga aaa gaa gtt act cgt caa aag atg agc tta<br>Ile Ile Leu Asn Asn Gly Lys Glu Val Thr Arg Gln Lys Met Ser Leu<br>                  520                        525                       530 | 1759 |
| acc gcc cgt cca gat gta gca gca gta tat cct tca ctt tat aat agt<br>Thr Ala Arg Pro Asp Val Ala Ala Val Tyr Pro Ser Leu Tyr Asn Ser<br>535                                  540                        545 | 1807 |
| gct gtt agt ggt ttt gac act act att aaa ttg act aat gat caa tat<br>Ala Val Ser Gly Phe Asp Thr Thr Ile Lys Leu Thr Asn Asp Gln Tyr<br>550                                  555                        560                       565 | 1855 |
| caa gcg ctt aat ggc caa tta caa gta ttg tta cgt ttt tct aaa gct<br>Gln Ala Leu Asn Gly Gln Leu Gln Val Leu Leu Arg Phe Ser Lys Ala<br>                     570                        575                       580 | 1903 |
| gct gat ggt aat cca agt ggt gat aat act gta act gat caa ttt agt<br>Ala Asp Gly Asn Pro Ser Gly Asp Asn Thr Val Thr Asp Gln Phe Ser<br>                       585                        590                       595 | 1951 |
| aaa aat tat gca act act gga gga aac ttt gac tat gta aaa gta aat<br>Lys Asn Tyr Ala Thr Thr Gly Gly Asn Phe Asp Tyr Val Lys Val Asn<br>                     600                        605                       610 | 1999 |
| ggt aat caa gtt gaa ttt agt ggt tgg cac gca act aac caa tca aat<br>Gly Asn Gln Val Glu Phe Ser Gly Trp His Ala Thr Asn Gln Ser Asn | 2047 |

```
                -continued
    615              620              625
gat aaa gat tca caa tgg att att gtt tta gtt aat ggt aag gaa gta    2095
Asp Lys Asp Ser Gln Trp Ile Ile Val Leu Val Asn Gly Lys Glu Val
630             635              640              645 aag cgt caa tta gtt aat gat act aaa gag gga gct gct ggc ttc aac    2143
Lys Arg Gln Leu Val Asn Asp Thr Lys Glu Gly Ala Ala Gly Phe Asn
            650              655              660 cga aac gat gtc tac aaa gta aat cca gct att gaa aac agt tct atg    2191
Arg Asn Asp Val Tyr Lys Val Asn Pro Ala Ile Glu Asn Ser Ser Met
        665              670              675 tct gga ttc caa ggc att att act tta cct gtg aca gtt aaa aac gaa    2239
Ser Gly Phe Gln Gly Ile Ile Thr Leu Pro Val Thr Val Lys Asn Glu
    680              685              690 aat gtc caa ctt gtt cat cgg ttt agt aac gat gtg aag act ggt gaa    2287
Asn Val Gln Leu Val His Arg Phe Ser Asn Asp Val Lys Thr Gly Glu
695              700              705 ggt aac tat gtt gat ttc tgg tca gag cta atg cct gtt aag gat agc    2335
Gly Asn Tyr Val Asp Phe Trp Ser Glu Leu Met Pro Val Lys Asp Ser
710              715              720              725 ttc caa aag ggg aat ggc cca ctt aag caa ttt ggc tta caa act att    2383
Phe Gln Lys Gly Asn Gly Pro Leu Lys Gln Phe Gly Leu Gln Thr Ile
            730              735              740 aac ggt caa caa tat tat att gac cca aca act ggt caa cca cgt aag    2431
Asn Gly Gln Gln Tyr Tyr Ile Asp Pro Thr Thr Gly Gln Pro Arg Lys
        745              750              755 aat ttc tta tta caa agt gga aat aat tgg att tac ttt gat agt gat    2479
Asn Phe Leu Leu Gln Ser Gly Asn Asn Trp Ile Tyr Phe Asp Ser Asp
    760              765              770 act ggt gtg ggt act aat gca ctt gaa tta caa ttt gca aag gga act    2527
Thr Gly Val Gly Thr Asn Ala Leu Glu Leu Gln Phe Ala Lys Gly Thr
775              780              785 gtt tca tct aat gaa caa tac cgt aac ggt aat gca gct tac agt tat    2575
Val Ser Ser Asn Glu Gln Tyr Arg Asn Gly Asn Ala Ala Tyr Ser Tyr
790              795              800              805 gat gac aag agt atc gaa aat gta aat ggt tac tta aca gca gat aca    2623
Asp Asp Lys Ser Ile Glu Asn Val Asn Gly Tyr Leu Thr Ala Asp Thr
            810              815              820 tgg tac cgt cca aaa cag atc tta aag gat gga act acc tgg act gac    2671
Trp Tyr Arg Pro Lys Gln Ile Leu Lys Asp Gly Thr Thr Trp Thr Asp
        825              830              835 tca aaa gaa aca gat atg cga cca atc ttg atg gta tgg tgg cct aat    2719
Ser Lys Glu Thr Asp Met Arg Pro Ile Leu Met Val Trp Trp Pro Asn
    840              845              850 act ctt acc caa gca tac tac ctt aat tac atg aaa caa cat ggt aat    2767
Thr Leu Thr Gln Ala Tyr Tyr Leu Asn Tyr Met Lys Gln His Gly Asn
855              860              865 tta tta cca tct gct tta cca ttc ttt aat gcg gat gct gat cct gca    2815
Leu Leu Pro Ser Ala Leu Pro Phe Phe Asn Ala Asp Ala Asp Pro Ala
870              875              880              885 gaa tta aat cat tat tcc gaa att gtg caa caa aat att gaa aaa cga    2863
Glu Leu Asn His Tyr Ser Glu Ile Val Gln Gln Asn Ile Glu Lys Arg
            890              895              900 att agt gaa acc gga aat act gat tgg tta cgt act tta atg cac gat    2911
Ile Ser Glu Thr Gly Asn Thr Asp Trp Leu Arg Thr Leu Met His Asp
        905              910              915 ttt gtt act aac aat ccg atg tgg aat aag gat agt gaa aat gtt aac    2959
Phe Val Thr Asn Asn Pro Met Trp Asn Lys Asp Ser Glu Asn Val Asn
    920              925              930 ttt agt ggt att caa ttc caa ggc gga ttc tta aag tat gaa aac tca    3007
```

```
              Phe Ser Gly Ile Gln Phe Gln Gly Gly Phe Leu Lys Tyr Glu Asn Ser
                  935                 940                 945 gat tta acg cct tat gct aac tct gat tat cgc tta ctt ggt cgg atg              3055
Asp Leu Thr Pro Tyr Ala Asn Ser Asp Tyr Arg Leu Leu Gly Arg Met
950                 955                 960                 965 cca atc aat att aag gat caa aca tat cgg gga caa gaa ttc cta ctt              3103
Pro Ile Asn Ile Lys Asp Gln Thr Tyr Arg Gly Gln Glu Phe Leu Leu
                970                 975                 980 gct aac gat att gat aac tct aat cct gtt gtt caa gca gaa caa tta              3151
Ala Asn Asp Ile Asp Asn Ser Asn Pro Val Val Gln Ala Glu Gln Leu
            985                 990                 995 aac tgg tta tac tat ctc ttg aac ttt gga acg atc aca gct aat aat              3199
Asn Trp Leu Tyr Tyr Leu Leu Asn Phe Gly Thr Ile Thr Ala Asn Asn
       1000                1005                1010 gat caa gct aat ttt gat tct gta cgg gta gat gca ccg gat aat att              3247
Asp Gln Ala Asn Phe Asp Ser Val Arg Val Asp Ala Pro Asp Asn Ile
   1015                1020                1025 gat gcc gat ctt atg aat atc gct cag gac tac ttt aat gct gca tat              3295
Asp Ala Asp Leu Met Asn Ile Ala Gln Asp Tyr Phe Asn Ala Ala Tyr
1030                1035                1040                1045 ggt atg gac tca gat gct gtc tca aat aag cat att aat att ctt gaa              3343
Gly Met Asp Ser Asp Ala Val Ser Asn Lys His Ile Asn Ile Leu Glu
                1050                1055                1060 gac tgg aat cat gct gat ccg gaa tac ttt aat aag atc gga aat cca              3391
Asp Trp Asn His Ala Asp Pro Glu Tyr Phe Asn Lys Ile Gly Asn Pro
            1065                1070                1075 caa ttg aca atg gat gat act att aag aat tcc ctg aat cat ggg ctt              3439
Gln Leu Thr Met Asp Asp Thr Ile Lys Asn Ser Leu Asn His Gly Leu
       1080                1085                1090 tca gat gca act aat cgt tgg gga tta gat gca att gtt cat cag tca              3487
Ser Asp Ala Thr Asn Arg Trp Gly Leu Asp Ala Ile Val His Gln Ser
   1095                1100                1105 tta gct gat cgt gaa aat aat tcc acg gaa aat gtt gta att cct aat              3535
Leu Ala Asp Arg Glu Asn Asn Ser Thr Glu Asn Val Val Ile Pro Asn
1110                1115                1120                1125 tac agt ttc gtt cgg gct cac gat aat aat tct caa gat caa att caa              3583
Tyr Ser Phe Val Arg Ala His Asp Asn Asn Ser Gln Asp Gln Ile Gln
                1130                1135                1140 aat gct att cgt gat gta aca ggc aaa gat tac cat act ttc act ttt              3631
Asn Ala Ile Arg Asp Val Thr Gly Lys Asp Tyr His Thr Phe Thr Phe
            1145                1150                1155 gaa gat gag caa aag ggt att gat gcg tac att caa gat caa aat tca              3679
Glu Asp Glu Gln Lys Gly Ile Asp Ala Tyr Ile Gln Asp Gln Asn Ser
       1160                1165                1170 aca gtg aag aaa tat aac ctt tat aat att ccg gct tca tac gca att              3727
Thr Val Lys Lys Tyr Asn Leu Tyr Asn Ile Pro Ala Ser Tyr Ala Ile
   1175                1180                1185 ctt tta act aac aag gat aca att cca cgt gta tac tat ggt gac ttg              3775
Leu Leu Thr Asn Lys Asp Thr Ile Pro Arg Val Tyr Tyr Gly Asp Leu
1190                1195                1200                1205 tat act gat ggt ggc caa tac atg gaa cat caa aca cgt tac tat gat              3823
Tyr Thr Asp Gly Gly Gln Tyr Met Glu His Gln Thr Arg Tyr Tyr Asp
                1210                1215                1220 act tta acg aac ctg ctt aaa tca cga gtt aag tat gtt gcc ggt ggc              3871
Thr Leu Thr Asn Leu Leu Lys Ser Arg Val Lys Tyr Val Ala Gly Gly
            1225                1230                1235 caa tca atg caa aca atg agc gtt ggc ggc aat aat aac att tta act              3919
Gln Ser Met Gln Thr Met Ser Val Gly Gly Asn Asn Asn Ile Leu Thr
       1240                1245                1250
```

```
agt gtt cgt tat ggt aaa ggt gcg atg aca gct act gat act ggt act    3967
Ser Val Arg Tyr Gly Lys Gly Ala Met Thr Ala Thr Asp Thr Gly Thr
    1255                1260                1265 gat gaa acc aga aca caa ggt att ggg gtt gtt gta agt aat acg cca    4015
Asp Glu Thr Arg Thr Gln Gly Ile Gly Val Val Val Ser Asn Thr Pro
1270                1275                1280                1285 aat cta aag cta ggt gtc aac gat aaa gta gtt ctt cat atg gga gct    4063
Asn Leu Lys Leu Gly Val Asn Asp Lys Val Val Leu His Met Gly Ala
            1290                1295                1300 gcg cac aag aac caa caa tat cgg gca gcc gtg ttg acg aca act gat    4111
Ala His Lys Asn Gln Gln Tyr Arg Ala Ala Val Leu Thr Thr Thr Asp
        1305                1310                1315 gga gtc att aat tat act tct gat caa ggg gca ccg gtt gca atg act    4159
Gly Val Ile Asn Tyr Thr Ser Asp Gln Gly Ala Pro Val Ala Met Thr
    1320                1325                1330 gac gag aac ggt gat cta tac tta tct agt cat aac cta gtt gtt aat    4207
Asp Glu Asn Gly Asp Leu Tyr Leu Ser Ser His Asn Leu Val Val Asn
    1335                1340                1345 ggt aaa gaa gaa gca gat aca gct gtt caa ggt tat gct aac cct gat    4255
Gly Lys Glu Glu Ala Asp Thr Ala Val Gln Gly Tyr Ala Asn Pro Asp
1350                1355                1360                1365 gtt tca gga tat ctt gct gta tgg gta cca gtt gga gca agt gat aac    4303
Val Ser Gly Tyr Leu Ala Val Trp Val Pro Val Gly Ala Ser Asp Asn
            1370                1375                1380 caa gat gct cga act gct cca tct act gaa aag aat agt ggt aac tct    4351
Gln Asp Ala Arg Thr Ala Pro Ser Thr Glu Lys Asn Ser Gly Asn Ser
        1385                1390                1395 gca tac aga aca aat gct gct ttt gat tca aat gtt att ttt gaa gcc    4399
Ala Tyr Arg Thr Asn Ala Ala Phe Asp Ser Asn Val Ile Phe Glu Ala
    1400                1405                1410 ttt tct aac ttt gtc tat aca cca aca aag gaa agt gaa cgt gct aat    4447
Phe Ser Asn Phe Val Tyr Thr Pro Thr Lys Glu Ser Glu Arg Ala Asn
    1415                1420                1425 gtt cga att gcc caa aat gct gat ttc ttt gct tca tta ggt ttt act    4495
Val Arg Ile Ala Gln Asn Ala Asp Phe Phe Ala Ser Leu Gly Phe Thr
1430                1435                1440                1445 tct ttc gag atg gcg cca caa tat aat tca agt aaa gat cgc aca ttc    4543
Ser Phe Glu Met Ala Pro Gln Tyr Asn Ser Ser Lys Asp Arg Thr Phe
            1450                1455                1460 cta gat tca aca att gat aac gga tat gcg ttt act gat cgt tat gat    4591
Leu Asp Ser Thr Ile Asp Asn Gly Tyr Ala Phe Thr Asp Arg Tyr Asp
        1465                1470                1475 ctt gga atg agt gag cct aat aag tac gga aca gat gaa gat cta cgt    4639
Leu Gly Met Ser Glu Pro Asn Lys Tyr Gly Thr Asp Glu Asp Leu Arg
    1480                1485                1490 aat gcc att caa gcg ctc cat aaa gct ggc tta caa gta atg gcg gat    4687
Asn Ala Ile Gln Ala Leu His Lys Ala Gly Leu Gln Val Met Ala Asp
    1495                1500                1505 tgg gtt cct gac caa atc tat aac ctt cct gga aaa gaa gtt gct aca    4735
Trp Val Pro Asp Gln Ile Tyr Asn Leu Pro Gly Lys Glu Val Ala Thr
1510                1515                1520                1525 gtc act cga gta gat gat cgt ggt aat gta tgg aaa gat gct atc att    4783
Val Thr Arg Val Asp Asp Arg Gly Asn Val Trp Lys Asp Ala Ile Ile
            1530                1535                1540 aat aat aat ctg tat gtt gtt aat act att ggt ggt ggc gaa tac cag    4831
Asn Asn Asn Leu Tyr Val Val Asn Thr Ile Gly Gly Gly Glu Tyr Gln
        1545                1550                1555 aag aag tat ggt gga gca ttc ctc gat aag tta caa aaa ctt tat cct    4879
Lys Lys Tyr Gly Gly Ala Phe Leu Asp Lys Leu Gln Lys Leu Tyr Pro
    1560                1565                1570
```

```
gaa atc ttc aca aag aag caa gtt tca act ggt gtt gct att gat cct      4927
Glu Ile Phe Thr Lys Lys Gln Val Ser Thr Gly Val Ala Ile Asp Pro
    1575                1580                1585 tca caa aag ata act gaa tgg tca gca aaa tac ttt aat gga aca aac      4975
Ser Gln Lys Ile Thr Glu Trp Ser Ala Lys Tyr Phe Asn Gly Thr Asn
1590                1595                1600                1605 att ctc cat cgt ggt tct ggt tat gta cta aaa gct gat ggt ggt caa      5023
Ile Leu His Arg Gly Ser Gly Tyr Val Leu Lys Ala Asp Gly Gly Gln
                1610                1615                1620 tac tac aac tta ggt act act aca aag caa ttc ttg cca att caa tta      5071
Tyr Tyr Asn Leu Gly Thr Thr Thr Lys Gln Phe Leu Pro Ile Gln Leu
            1625                1630                1635 act ggt gaa aag aaa caa gga aat gaa ggc ttt gtt aag ggt aat gat      5119
Thr Gly Glu Lys Lys Gln Gly Asn Glu Gly Phe Val Lys Gly Asn Asp
        1640                1645                1650 gga aat tac tac ttc tat gac tta gca ggt aat atg gtt aag aat acc      5167
Gly Asn Tyr Tyr Phe Tyr Asp Leu Ala Gly Asn Met Val Lys Asn Thr
    1655                1660                1665 ttt att gaa gat agt gtt ggc aac tgg tac ttc ttt gac caa gat ggt      5215
Phe Ile Glu Asp Ser Val Gly Asn Trp Tyr Phe Phe Asp Gln Asp Gly
1670                1675                1680                1685 aag atg gtt gaa aat aaa cat ttc gtt gat gtt gat tct tat ggt gaa      5263
Lys Met Val Glu Asn Lys His Phe Val Asp Val Asp Ser Tyr Gly Glu
                1690                1695                1700 aaa ggt act tac ttc ttc ttg aag aat ggt gta tca ttc cgt ggg gga      5311
Lys Gly Thr Tyr Phe Phe Leu Lys Asn Gly Val Ser Phe Arg Gly Gly
            1705                1710                1715 tta gtg caa act gac aat ggt act tat tac ttt gat aat tat gga aag      5359
Leu Val Gln Thr Asp Asn Gly Thr Tyr Tyr Phe Asp Asn Tyr Gly Lys
        1720                1725                1730 atg gta cgt aat caa act att aat gca ggt gcc atg att tat acc tta      5407
Met Val Arg Asn Gln Thr Ile Asn Ala Gly Ala Met Ile Tyr Thr Leu
    1735                1740                1745 gat gaa aac ggt aag ctt ata aag gct agt tat aat tca gat gcc gaa      5455
Asp Glu Asn Gly Lys Leu Ile Lys Ala Ser Tyr Asn Ser Asp Ala Glu
1750                1755                1760                1765 tat cca act tca act gat gtt ggt aag atg ctt gat caa aat aaa cta      5503
Tyr Pro Thr Ser Thr Asp Val Gly Lys Met Leu Asp Gln Asn Lys Leu
                1770                1775                1780 taaatggaaa taattagctg atttccgttt cttagaatcg aaagatttaa taactggggt    5563
taaaacggcc ctacaaaatc tgatattgat atagagatat tatttcctat atcaatatca    5623 gattttgct  ttttataaaa ttgattgtga ctaataagaa tccggaagat aacgttgttg    5683
ttatatcagt ggatttaagc aacatgaatt aattgaagat gacggcaatg attaaaagtc    5743
ggtctgatga ttattgatgt attactagta tttggttttt atcatttata tttttactgt    5803
tattggtgtc atatattcca caataacagt aaaggtatat atgctagttt attttttaag    5863
taattataat attctgatta taatttggaa atattcgctt ttagcaaaaa ggtagtaaac    5923
agatcagaat cgtcattctg cttttctact actaaaagtc tgtttttaaat tctaaactaa    5983 aataggctaa acactgatgt ttatcattta tattttttact gtt                     6026

<210> SEQ ID NO 2
<211> LENGTH: 1781
<212> TYPE: PRT
<213> ORGANISM: Lactobacillus reuteri

<400> SEQUENCE: 2
```

-continued

```
Met Glu Ile Lys Lys His Phe Lys Leu Tyr Lys Ser Gly Lys Gln Trp
 1               5                  10                  15

Val Thr Ala Ala Val Ala Thr Val Ala Val Ser Thr Ala Leu Leu Tyr
                20                  25                  30

Gly Gly Val Ala His Ala Asp Gln Gln Val Gln Gln Ala Ser Thr Thr
             35                  40                  45

Gln Asp Gln Thr Ser Thr Val Asn Asn Asp Thr Asp Lys Thr Val Ala
     50                  55                  60

Leu Asp Thr Asn Thr Asp Gln Ser Ala Gln Thr Thr Asp Lys Lys Gln
 65                  70                  75                  80

Val Val Ser Asn Thr Asn Gln Ser Lys Thr Asp Asp Thr Ser Thr Ala
                 85                  90                  95

Asp Lys Asn Ser Thr Ser Thr Pro Val Ser Val Leu Pro Ser Asn Asn
                100                 105                 110

Thr Glu Lys Gln Ala Lys Asn Tyr Asn Glu Gln Asp Lys Gly Asn Tyr
             115                 120                 125

Gly Asn Ile Asp Thr Ala Tyr Phe Ser Asn Asn Gln Leu His Val Ser
     130                 135                 140

Gly Trp Asn Ala Thr Asn Ala Ser Gln Gly Thr Asn Ser Arg Gln Ile
145                 150                 155                 160

Ile Val Arg Asp Ile Thr Thr Asn Asn Glu Leu Gly Arg Thr Asp Val
                165                 170                 175

Thr Asn Asn Val Ala Arg Pro Asp Val Lys Asn Val His Asn Val Tyr
            180                 185                 190

Asn Ala Asp Asn Ser Gly Phe Asp Val Asn Val Asn Ile Asp Phe Ser
        195                 200                 205

Lys Met Lys Asp Tyr Arg Asp Ser Ile Glu Ile Val Ser Arg Tyr Ser
    210                 215                 220

Gly Asn Gly Lys Ser Val Asp Trp Trp Ser Gln Pro Ile Thr Phe Asp
225                 230                 235                 240

Lys Asn Asn Tyr Ala Tyr Leu Asp Thr Phe Glu Val Lys Asn Gly Glu
                245                 250                 255

Leu His Ala Thr Gly Trp Asn Ala Thr Asn Ser Ala Ile Asn Tyr Asn
            260                 265                 270

His His Phe Val Ile Leu Phe Asp Gln Thr Asn Gly Lys Glu Val Ala
        275                 280                 285

Arg Gln Glu Val Arg Glu Gly Gln Ser Arg Pro Asp Val Ala Lys Val
    290                 295                 300

Tyr Pro Gln Val Val Gly Ala Ala Asn Ser Gly Phe Asn Val Thr Phe
305                 310                 315                 320

Asn Ile Ser Asp Leu Asp Tyr Thr His Gln Tyr Gln Val Leu Ser Arg
                325                 330                 335

Tyr Ser Asn Ser Asp Asn Gly Glu Gly Asp Asn Val Thr Tyr Trp Phe
            340                 345                 350

Asn Pro Gln Ser Ile Ala Pro Ala Asn Gln Ser Asn Gln Gly Tyr Leu
        355                 360                 365

Asp Ser Phe Asp Ile Ser Lys Asn Gly Glu Val Thr Val Thr Gly Trp
    370                 375                 380

Asn Ala Thr Asp Leu Ser Glu Leu Gln Asn Asn His Tyr Val Ile Leu
385                 390                 395                 400

Phe Asp Gln Thr Ala Gly Lys Gln Val Ala Ser Ala Lys Ala Asp Leu
                405                 410                 415

Ile Ser Arg Pro Asp Val Ala Lys Ala Tyr Pro Thr Val Lys Thr Ala
```

-continued

```
                420             425             430
Thr Asn Ser Gly Phe Lys Val Thr Phe Lys Val Asn Asn Leu Gln Pro
            435             440             445
Gly His Gln Tyr Ser Val Val Ser Arg Phe Ser Ala Asp Glu Asn Gly
        450             455             460
Asn Gly Asn Asp Lys Arg His Thr Asp Tyr Trp Phe Ser Pro Val Ile
465             470             475             480
Leu Asn Gln Thr Ala Ser Asn Ile Asp Thr Ile Thr Met Thr Ser Asn
                485             490             495
Gly Leu His Ile Ala Gly Trp Met Ala Ser Asp Asn Ser Ile Asn Glu
            500             505             510
Thr Thr Pro Tyr Ala Ile Ile Leu Asn Asn Gly Lys Glu Val Thr Arg
        515             520             525
Gln Lys Met Ser Leu Thr Ala Arg Pro Asp Val Ala Ala Val Tyr Pro
    530             535             540
Ser Leu Tyr Asn Ser Ala Val Ser Gly Phe Asp Thr Thr Ile Lys Leu
545             550             555             560
Thr Asn Asp Gln Tyr Gln Ala Leu Asn Gly Gln Leu Gln Val Leu Leu
                565             570             575
Arg Phe Ser Lys Ala Ala Asp Gly Asn Pro Ser Gly Asp Asn Thr Val
            580             585             590
Thr Asp Gln Phe Ser Lys Asn Tyr Ala Thr Thr Gly Gly Asn Phe Asp
        595             600             605
Tyr Val Lys Val Asn Gly Asn Gln Val Glu Phe Ser Gly Trp His Ala
    610             615             620
Thr Asn Gln Ser Asn Asp Lys Asp Ser Gln Trp Ile Ile Val Leu Val
625             630             635             640
Asn Gly Lys Glu Val Lys Arg Gln Leu Val Asn Asp Thr Lys Glu Gly
                645             650             655
Ala Ala Gly Phe Asn Arg Asn Asp Val Tyr Lys Val Asn Pro Ala Ile
            660             665             670
Glu Asn Ser Ser Met Ser Gly Phe Gln Gly Ile Ile Thr Leu Pro Val
        675             680             685
Thr Val Lys Asn Glu Asn Val Gln Leu Val His Arg Phe Ser Asn Asp
    690             695             700
Val Lys Thr Gly Glu Gly Asn Tyr Val Asp Phe Trp Ser Glu Leu Met
705             710             715             720
Pro Val Lys Asp Ser Phe Gln Lys Gly Asn Gly Pro Leu Lys Gln Phe
                725             730             735
Gly Leu Gln Thr Ile Asn Gly Gln Gln Tyr Tyr Ile Asp Pro Thr Thr
            740             745             750
Gly Gln Pro Arg Lys Asn Phe Leu Leu Gln Ser Gly Asn Asn Trp Ile
        755             760             765
Tyr Phe Asp Ser Asp Thr Gly Val Gly Thr Asn Ala Leu Glu Leu Gln
    770             775             780
Phe Ala Lys Gly Thr Val Ser Ser Asn Glu Gln Tyr Arg Asn Gly Asn
785             790             795             800
Ala Ala Tyr Ser Tyr Asp Asp Lys Ser Ile Glu Asn Val Asn Gly Tyr
                805             810             815
Leu Thr Ala Asp Thr Trp Tyr Arg Pro Lys Gln Ile Leu Lys Asp Gly
            820             825             830
Thr Thr Trp Thr Asp Ser Lys Glu Thr Asp Met Arg Pro Ile Leu Met
        835             840             845
```

-continued

```
Val Trp Trp Pro Asn Thr Leu Thr Gln Ala Tyr Tyr Leu Asn Tyr Met
    850                 855                 860

Lys Gln His Gly Asn Leu Leu Pro Ser Ala Leu Pro Phe Phe Asn Ala
865                 870                 875                 880

Asp Ala Asp Pro Ala Glu Leu Asn His Tyr Ser Glu Ile Val Gln Gln
                885                 890                 895

Asn Ile Glu Lys Arg Ile Ser Thr Gly Asn Thr Asp Trp Leu Arg
        900                 905                 910

Thr Leu Met His Asp Phe Val Thr Asn Asn Pro Met Trp Asn Lys Asp
        915                 920                 925

Ser Glu Asn Val Asn Phe Ser Gly Ile Gln Phe Gln Gly Gly Phe Leu
    930                 935                 940

Lys Tyr Glu Asn Ser Asp Leu Thr Pro Tyr Ala Asn Ser Asp Tyr Arg
945                 950                 955                 960

Leu Leu Gly Arg Met Pro Ile Asn Ile Lys Asp Gln Thr Tyr Arg Gly
                965                 970                 975

Gln Glu Phe Leu Leu Ala Asn Asp Ile Asp Asn Ser Asn Pro Val Val
            980                 985                 990

Gln Ala Glu Gln Leu Asn Trp Leu Tyr Tyr Leu Leu Asn Phe Gly Thr
        995                 1000                1005

Ile Thr Ala Asn Asn Asp Gln Ala Asn Phe Asp Ser Val Arg Val Asp
    1010                1015                1020

Ala Pro Asp Asn Ile Asp Ala Asp Leu Met Asn Ile Ala Gln Asp Tyr
1025                1030                1035                1040

Phe Asn Ala Ala Tyr Gly Met Asp Ser Asp Ala Val Ser Asn Lys His
                1045                1050                1055

Ile Asn Ile Leu Glu Asp Trp Asn His Ala Asp Pro Glu Tyr Phe Asn
            1060                1065                1070

Lys Ile Gly Asn Pro Gln Leu Thr Met Asp Asp Thr Ile Lys Asn Ser
        1075                1080                1085

Leu Asn His Gly Leu Ser Asp Ala Thr Asn Arg Trp Gly Leu Asp Ala
    1090                1095                1100

Ile Val His Gln Ser Leu Ala Asp Arg Glu Asn Asn Ser Thr Glu Asn
1105                1110                1115                1120

Val Val Ile Pro Asn Tyr Ser Phe Val Arg Ala His Asp Asn Asn Ser
                1125                1130                1135

Gln Asp Gln Ile Gln Asn Ala Ile Arg Asp Val Thr Gly Lys Asp Tyr
            1140                1145                1150

His Thr Phe Thr Phe Glu Asp Glu Gln Lys Gly Ile Asp Ala Tyr Ile
        1155                1160                1165

Gln Asp Gln Asn Ser Thr Val Lys Lys Tyr Asn Leu Tyr Asn Ile Pro
    1170                1175                1180

Ala Ser Tyr Ala Ile Leu Leu Thr Asn Lys Asp Thr Ile Pro Arg Val
1185                1190                1195                1200

Tyr Tyr Gly Asp Leu Tyr Thr Asp Gly Gly Gln Tyr Met Glu His Gln
                1205                1210                1215

Thr Arg Tyr Tyr Asp Thr Leu Thr Asn Leu Leu Lys Ser Arg Val Lys
            1220                1225                1230

Tyr Val Ala Gly Gly Gln Ser Met Gln Thr Met Ser Val Gly Gly Asn
        1235                1240                1245

Asn Asn Ile Leu Thr Ser Val Arg Tyr Gly Lys Gly Ala Met Thr Ala
    1250                1255                1260
```

-continued

```
Thr Asp Thr Gly Thr Asp Glu Thr Arg Thr Gln Gly Ile Gly Val Val
1265                1270                1275                1280

Val Ser Asn Thr Pro Asn Leu Lys Leu Gly Val Asn Asp Lys Val Val
            1285                1290                1295

Leu His Met Gly Ala Ala His Lys Asn Gln Gln Tyr Arg Ala Ala Val
            1300                1305                1310

Leu Thr Thr Thr Asp Gly Val Ile Asn Tyr Thr Ser Asp Gln Gly Ala
        1315                1320                1325

Pro Val Ala Met Thr Asp Glu Asn Gly Asp Leu Tyr Leu Ser Ser His
        1330                1335                1340

Asn Leu Val Val Asn Gly Lys Glu Glu Ala Asp Thr Ala Val Gln Gly
1345                1350                1355                1360

Tyr Ala Asn Pro Asp Val Ser Gly Tyr Leu Ala Val Trp Val Pro Val
            1365                1370                1375

Gly Ala Ser Asp Asn Gln Asp Ala Arg Thr Ala Pro Ser Thr Glu Lys
            1380                1385                1390

Asn Ser Gly Asn Ser Ala Tyr Arg Thr Asn Ala Ala Phe Asp Ser Asn
        1395                1400                1405

Val Ile Phe Glu Ala Phe Ser Asn Phe Val Tyr Thr Pro Thr Lys Glu
    1410                1415                1420

Ser Glu Arg Ala Asn Val Arg Ile Ala Gln Asn Ala Asp Phe Phe Ala
1425                1430                1435                1440

Ser Leu Gly Phe Thr Ser Phe Glu Met Ala Pro Gln Tyr Asn Ser Ser
            1445                1450                1455

Lys Asp Arg Thr Phe Leu Asp Ser Thr Ile Asp Asn Gly Tyr Ala Phe
            1460                1465                1470

Thr Asp Arg Tyr Asp Leu Gly Met Ser Glu Pro Asn Lys Tyr Gly Thr
        1475                1480                1485

Asp Glu Asp Leu Arg Asn Ala Ile Gln Ala Leu His Lys Ala Gly Leu
    1490                1495                1500

Gln Val Met Ala Asp Trp Val Pro Asp Gln Ile Tyr Asn Leu Pro Gly
1505                1510                1515                1520

Lys Glu Val Ala Thr Val Thr Arg Val Asp Asp Arg Gly Asn Val Trp
            1525                1530                1535

Lys Asp Ala Ile Ile Asn Asn Asn Leu Tyr Val Val Asn Thr Ile Gly
            1540                1545                1550

Gly Gly Glu Tyr Gln Lys Lys Tyr Gly Gly Ala Phe Leu Asp Lys Leu
        1555                1560                1565

Gln Lys Leu Tyr Pro Glu Ile Phe Thr Lys Lys Gln Val Ser Thr Gly
    1570                1575                1580

Val Ala Ile Asp Pro Ser Gln Lys Ile Thr Glu Trp Ser Ala Lys Tyr
1585                1590                1595                1600

Phe Asn Gly Thr Asn Ile Leu His Arg Gly Ser Gly Tyr Val Leu Lys
            1605                1610                1615

Ala Asp Gly Gly Gln Tyr Tyr Asn Leu Gly Thr Thr Thr Lys Gln Phe
            1620                1625                1630

Leu Pro Ile Gln Leu Thr Gly Glu Lys Lys Gln Gly Asn Glu Gly Phe
        1635                1640                1645

Val Lys Gly Asn Asp Gly Asn Tyr Tyr Phe Tyr Asp Leu Ala Gly Asn
    1650                1655                1660

Met Val Lys Asn Thr Phe Ile Glu Asp Ser Val Gly Asn Trp Tyr Phe
1665                1670                1675                1680

Phe Asp Gln Asp Gly Lys Met Val Glu Asn Lys His Phe Val Asp Val
```

```
                        1685              1690              1695
Asp Ser Tyr Gly Glu Lys Gly Thr Tyr Phe Phe Leu Lys Asn Gly Val
            1700              1705              1710

Ser Phe Arg Gly Gly Leu Val Gln Thr Asp Asn Gly Thr Tyr Tyr Phe
        1715              1720              1725

Asp Asn Tyr Gly Lys Met Val Arg Asn Gln Thr Ile Asn Ala Gly Ala
    1730              1735              1740

Met Ile Tyr Thr Leu Asp Glu Asn Gly Lys Leu Ile Lys Ala Ser Tyr
1745              1750              1755              1760

Asn Ser Asp Ala Glu Tyr Pro Thr Ser Thr Asp Val Gly Lys Met Leu
            1765              1770              1775

Asp Gln Asn Lys Leu
        1780

<210> SEQ ID NO 3
<211> LENGTH: 13
<212> TYPE: PRT
<213> ORGANISM: Lactobacillus reuteri

<400> SEQUENCE: 3

Tyr Tyr Phe Tyr Asp Leu Ala Gly Asn Met Val Lys Asn
1               5                   10

<210> SEQ ID NO 4
<211> LENGTH: 13
<212> TYPE: PRT
<213> ORGANISM: Lactobacillus reuteri

<400> SEQUENCE: 4

Trp Tyr Phe Phe Asp Gln Asp Gly Lys Met Val Glu Asn
1               5                   10

<210> SEQ ID NO 5
<211> LENGTH: 13
<212> TYPE: PRT
<213> ORGANISM: Lactobacillus reuteri

<400> SEQUENCE: 5

Thr Tyr Tyr Phe Asp Asn Tyr Gly Lys Met Val Arg Asn
1               5                   10

<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (9)
<223> OTHER INFORMATION: a, t, c or g
<220> FEATURE:
<221> NAME/KEY: modified_base
<222> LOCATION: (15)
<223> OTHER INFORMATION: a, t, c or g
<220> FEATURE:
<221> NAME/KEY: modified_base
<222> LOCATION: (18)
<223> OTHER INFORMATION: a, t, c or g
<220> FEATURE:
<221> NAME/KEY: modified_base
<222> LOCATION: (21)
<223> OTHER INFORMATION: a, t, c or g

<400> SEQUENCE: 6
```

-continued gayaakwsna aksynrtngt nsargc                                26

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (2)
<223> OTHER INFORMATION: a, t, c or g
<220> FEATURE:
<221> NAME/KEY: modified_base
<222> LOCATION: (5)
<223> OTHER INFORMATION: a, t, c or g
<220> FEATURE:
<221> NAME/KEY: modified_base
<222> LOCATION: (8)
<223> OTHER INFORMATION: a, t, c or g
<220> FEATURE:
<221> NAME/KEY: modified_base
<222> LOCATION: (17)
<223> OTHER INFORMATION: a, t, c or g
<220> FEATURE:
<221> NAME/KEY: modified_base
<222> LOCATION: (21)
<223> OTHER INFORMATION: a, t, c or g

<400> SEQUENCE: 7
gnkcncanat ratrccnctr na                                    22

<210> SEQ ID NO 8
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 8
acaaccacca tggaattagg tcgcactgat gtaac                      35

<210> SEQ ID NO 9
<211> LENGTH: 47
<212> TYPE: DNA
<213> ORGANISM: Artificial Sequence
<220> FEATURE:
<223> OTHER INFORMATION: Description of Artificial Sequence: Primer

<400> SEQUENCE: 9
gccagctgga tccgtcgact agtttatttt tgatcaagca tcttacc         47

<210> SEQ ID NO 10
<211> LENGTH: 545
<212> TYPE: PRT
<213> ORGANISM: Streptococcus mutans

<400> SEQUENCE: 10

Leu Leu Ala Asn Asp Ile Asp Asn Ser Asn Pro Val Val Gln Ala Glu
 1               5                  10                  15

Gln Leu Asn Trp Leu His Tyr Leu Met Asn Tyr Gly Ser Ile Val Ala
            20                  25                  30

Asn Asp Pro Glu Ala Asn Phe Asp Gly Val Arg Val Asp Ala Val Asp
        35                  40                  45

Asn Val Asn Ala Asp Leu Leu Gln Ile Ala Ser Asp Tyr Leu Lys Ala
    50                  55                  60

His Tyr Gly Val Asp Lys Ser Glu Lys Asn Ala Ile Asn His Leu Ser

-continued

```
             65                  70                  75                  80
Ile Leu Glu Ala Trp Ser Asp Asn Asp Pro Gln Tyr Asn Lys Asp Thr
                     85                  90                  95
Lys Gly Ala Gln Leu Pro Ile Asp Asn Lys Leu Arg Leu Ser Leu Leu
                100                 105                 110
Tyr Ala Leu Thr Arg Pro Leu Glu Lys Asp Ala Ser Asn Lys Asn Glu
                115                 120                 125
Ile Arg Ser Gly Leu Glu Pro Val Ile Thr Asn Ser Leu Asn Asn Arg
                130                 135                 140
Ser Ala Glu Gly Lys Asn Ser Glu Arg Met Ala Asn Tyr Ile Phe Ile
145                 150                 155                 160
Arg Ala His Asp Ser Glu Val Gln Thr Val Ile Ala Lys Ile Ile Lys
                165                 170                 175
Ala Gln Ile Asn Pro Lys Thr Asp Gly Leu Thr Phe Thr Leu Asp Glu
                180                 185                 190
Leu Lys Gln Ala Phe Lys Ile Tyr Asn Glu Asp Met Arg Gln Ala Lys
                195                 200                 205
Lys Lys Tyr Thr Gln Ser Asn Ile Pro Thr Ala Tyr Ala Leu Met Leu
                210                 215                 220
Ser Asn Lys Asp Ser Ile Thr Arg Leu Tyr Tyr Gly Asp Met Tyr Ser
225                 230                 235                 240
Asp Asp Gly Gln Tyr Met Ala Thr Lys Ser Pro Tyr Tyr Asp Ala Ile
                245                 250                 255
Asp Thr Leu Leu Lys Ala Arg Ile Lys Tyr Ala Ala Gly Gly Gln Asp
                260                 265                 270
Met Lys Ile Thr Tyr Val Glu Gly Asp Lys Ser His Met Asp Trp Asp
                275                 280                 285
Tyr Thr Gly Val Leu Thr Ser Val Arg Tyr Gly Thr Gly Ala Asn Glu
                290                 295                 300
Ala Thr Asp Gln Gly Ser Glu Ala Thr Lys Thr Gln Gly Met Ala Val
305                 310                 315                 320
Ile Thr Ser Asn Asn Pro Ser Leu Lys Leu Asn Gln Asn Asp Lys Val
                325                 330                 335
Ile Val Asn Met Gly Ala Ala His Lys Asn Gln Glu Tyr Arg Pro Leu
                340                 345                 350
Leu Leu Thr Thr Lys Asp Gly Leu Thr Ser Tyr Thr Ser Asp Ala Ala
                355                 360                 365
Ala Lys Ser Leu Tyr Arg Lys Thr Asn Asp Lys Gly Glu Leu Val Phe
                370                 375                 380
Asp Ala Ser Asp Ile Gln Gly Leu Tyr Leu Asn Pro Gln Val Ser Gly
385                 390                 395                 400
Leu Ala Val Trp Val Pro Val Gly Ala Ser Asp Asn Gln Asp Val Arg
                405                 410                 415
Val Ala Ala Ser Asn Lys Ala Asn Ala Thr Gly Gln Val Tyr Glu Ser
                420                 425                 430
Ser Ser Ala Leu Asp Ser Gln Leu Ile Tyr Glu Gly Phe Ser Asn Phe
                435                 440                 445
Gln Asp Phe Val Thr Lys Asp Ser Asp Tyr Thr Asn Lys Lys Ile Ala
                450                 455                 460
Gln Asn Val Gln Leu Phe Lys Ser Trp Gly Val Thr Ser Phe Glu Met
465                 470                 475                 480
Ala Pro Gln Tyr Val Ser Ser Glu Asp Gly Ser Phe Leu Asp Ser Ile
                485                 490                 495
```

```
Ile Gln Asn Gly Tyr Ala Phe Glu Asp Arg Tyr Asp Leu Ala Met Ser
            500                 505                 510
Lys Asn Asn Lys Tyr Gly Ser Gln Gln Asp Met Ile Asn Ala Val Lys
        515                 520                 525
Ala Leu His Lys Ser Gly Ile Gln Val Ile Ala Asp Trp Val Pro Asp
    530                 535                 540
Gln
545

<210> SEQ ID NO 11
<211> LENGTH: 522
<212> TYPE: PRT
<213> ORGANISM: Leuconostoc mesenteroides

<400> SEQUENCE: 11

Leu Leu Ala Asn Asp Val Asp Asn Ser Asn Val Val Glu Ala Glu
1               5                  10                  15
Gln Leu Asn Trp Leu Tyr Tyr Leu Met Asn Phe Gly Thr Ile Thr Ala
            20                  25                  30
Asn Asp Ala Asp Ala Asn Phe Asp Gly Ile Arg Val Asp Ala Val Asp
        35                  40                  45
Asn Val Asp Ala Asp Leu Leu Gln Ile Ala Ala Asp Tyr Phe Lys Leu
    50                  55                  60
Ala Tyr Gly Val Asp Gln Asn Asp Ala Thr Ala Asn Gln His Leu Ser
65                  70                  75                  80
Ile Leu Glu Asp Trp Ser His Asn Asp Pro Leu Tyr Val Thr Asp Gln
                85                  90                  95
Gly Ser Asn Gln Leu Thr Met Asp Asp Tyr Val His Thr Gln Leu Ile
            100                 105                 110
Trp Ser Leu Thr Lys Ser Ser Asp Ile Arg Gly Thr Met Gln Arg Phe
        115                 120                 125
Val Asp Tyr Tyr Met Val Asp Arg Ser Asn Asp Ser Thr Glu Asn Glu
    130                 135                 140
Ala Ile Pro Asn Tyr Ser Phe Val Arg Ala His Asp Ser Glu Val Gln
145                 150                 155                 160
Thr Val Ile Ala Gln Ile Val Ser Asp Leu Tyr Pro Asp Val Glu Asn
                165                 170                 175
Ser Leu Ala Pro Thr Thr Glu Gln Leu Ala Ala Ala Phe Lys Val Tyr
            180                 185                 190
Asn Glu Asp Glu Lys Leu Ala Asp Lys Lys Tyr Thr Gln Tyr Asn Met
        195                 200                 205
Ala Ser Ala Tyr Ala Met Leu Leu Thr Asn Lys Asp Thr Val Pro Arg
    210                 215                 220
Tyr Tyr Gly Asp Leu Tyr Thr Asp Asp Gly Gln Tyr Met Ala Thr Lys
225                 230                 235                 240
Ser Pro Tyr Tyr Asp Ala Ile Asn Thr Leu Leu Lys Ala Arg Val Gln
                245                 250                 255
Tyr Val Ala Gly Gly Gln Ser Met Ser Val Asp Ser Asn Asp Val Leu
            260                 265                 270
Thr Ser Val Arg Tyr Gly Lys Asp Ala Met Thr Ala Ser Asp Thr Gly
        275                 280                 285
Thr Ser Glu Thr Arg Thr Glu Gly Ile Gly Val Ile Val Ser Asn Asn
    290                 295                 300
Ala Glu Leu Gln Leu Glu Asp Gly His Thr Val Thr Leu His Met Gly
```

-continued

```
                305                 310                 315                 320
Ala Ala His Lys Asn Gln Ala Tyr Arg Ala Leu Leu Ser Thr Thr Ala
                    325                 330                 335

Asp Gly Leu Ala Tyr Tyr Asp Thr Asp Glu Asn Ala Pro Val Ala Tyr
                340                 345                 350

Thr Asp Ala Asn Gly Asp Leu Ile Phe Thr Asn Glu Ser Ile Tyr Gly
                355                 360                 365

Val Gln Asn Pro Gln Val Ser Gly Tyr Leu Ala Val Trp Val Pro Val
    370                 375                 380

Gly Ala Gln Gln Asp Gln Asp Ala Arg Thr Ala Ser Asp Thr Thr Thr
385                 390                 395                 400

Asn Thr Ser Asp Lys Val Phe His Ser Asn Ala Ala Leu Asp Ser Gln
                405                 410                 415

Val Ile Tyr Glu Gly Phe Ser Asn Phe Gln Ala Phe Ala Thr Asp Ser
                420                 425                 430

Ser Glu Tyr Thr Asn Val Val Ile Ala Gln Asn Ala Asp Gln Phe Lys
                435                 440                 445

Gln Trp Gly Val Thr Ser Phe Gln Leu Ala Pro Gln Tyr Arg Ser Ser
    450                 455                 460

Thr Asp Thr Ser Phe Leu Asp Ser Ile Ile Gln Asn Gly Tyr Ala Phe
465                 470                 475                 480

Thr Asp Arg Tyr Asp Leu Gly Tyr Gly Thr Pro Thr Lys Tyr Gly Thr
                485                 490                 495

Ala Asp Gln Leu Arg Asp Ala Ile Lys Ala Leu His Ala Ser Gly Ile
                500                 505                 510

Gln Ala Ile Ala Asp Trp Val Pro Asp Gln
    515                 520
```

<210> SEQ ID NO 12
<211> LENGTH: 584
<212> TYPE: PRT
<213> ORGANISM: Leuconostoc mesenteroides

<400> SEQUENCE: 12

```
Leu Leu Ala Asn Asp Ile Asp Asn Ser Asn Pro Ile Val Gln Ala Glu
  1               5                  10                  15

Gln Leu Asn Trp Leu His Tyr Leu Met Asn Phe Gly Ser Ile Thr Gly
                 20                  25                  30

Asn Asn Asp Asn Ala Asn Phe Asp Gly Ile Arg Val Asp Ala Val Asp
             35                  40                  45

Asn Val Asp Ala Asp Leu Leu Lys Ile Ala Gly Asp Tyr Phe Lys Ala
         50                  55                  60

Leu Tyr Gly Thr Asp Lys Ser Asp Ala Asn Ala Asn Lys His Leu Ser
 65                  70                  75                  80

Ile Leu Glu Asp Trp Asn Gly Lys Asp Pro Gln Tyr Val Asn Gln Gln
                 85                  90                  95

Gly Asn Ala Gln Leu Thr Met Asp Tyr Thr Val Thr Ser Gln Phe Gly
            100                 105                 110

Asn Ser Leu Thr His Gly Ala Asn Asn Arg Ser Asn Met Trp Tyr Phe
        115                 120                 125

Leu Asp Thr Gly Tyr Tyr Leu Asn Gly Asp Leu Asn Lys Lys Ile Val
    130                 135                 140

Asp Lys Asn Arg Pro Asn Ser Gly Thr Leu Val Asn Arg Ile Ala Asn
145                 150                 155                 160
```

-continued

```
Ser Gly Asp Thr Lys Val Ile Pro Asn Tyr Ser Phe Val Arg Ala His
            165                 170                 175
Asp Tyr Asp Ala Gln Asp Pro Ile Arg Lys Ala Met Ile Asp His Gly
        180                 185                 190
Ile Ile Lys Asn Met Gln Asp Thr Phe Thr Phe Asp Gln Leu Ala Gln
    195                 200                 205
Gly Met Glu Phe Tyr Tyr Lys Asp Gln Glu Asn Pro Ser Gly Phe Lys
210                 215                 220
Lys Tyr Asn Asp Tyr Asn Leu Pro Ser Ala Tyr Ala Met Leu Leu Thr
225                 230                 235                 240
Asn Lys Asp Thr Val Pro Arg Val Tyr Tyr Gly Asp Met Tyr Leu Glu
            245                 250                 255
Gly Gly Gln Tyr Met Glu Lys Gly Thr Ile Tyr Asn Pro Val Ile Ser
        260                 265                 270
Ala Leu Leu Lys Ala Arg Ile Lys Tyr Val Ser Gly Gly Gln Thr Met
    275                 280                 285
Ala Thr Asp Ser Ser Gly Lys Asp Leu Lys Asp Gly Glu Thr Asp Leu
290                 295                 300
Leu Thr Ser Val Arg Phe Gly Lys Gly Ile Met Thr Ser Asp Gln Thr
305                 310                 315                 320
Thr Thr Gln Asp Asn Ser Gln Asp Tyr Lys Asn Gln Gly Ile Gly Val
            325                 330                 335
Ile Val Gly Asn Asn Pro Asp Leu Lys Leu Asn Asn Asp Lys Thr Ile
        340                 345                 350
Thr Leu His Met Gly Lys Ala His Lys Asn Gln Leu Tyr Arg Ala Leu
    355                 360                 365
Val Leu Ser Asn Asp Ser Gly Ile Asp Val Tyr Asp Ser Asp Asp Lys
370                 375                 380
Ala Pro Thr Leu Arg Thr Asn Asp Asn Gly Asp Leu Ile Phe His Lys
385                 390                 395                 400
Thr Asn Thr Phe Val Lys Gln Asp Gly Thr Ile Ile Asn Tyr Glu Met
            405                 410                 415
Lys Gly Ser Leu Asn Ala Leu Ile Ser Gly Tyr Leu Gly Val Trp Val
        420                 425                 430
Pro Val Gly Ala Ser Asp Ser Gln Asp Ala Arg Thr Val Ala Thr Glu
    435                 440                 445
Ser Ser Ser Ser Asn Asp Gly Ser Val Phe His Ser Asn Ala Ala Leu
450                 455                 460
Asp Ser Asn Val Ile Tyr Glu Gly Phe Ser Asn Phe Gln Ala Met Pro
465                 470                 475                 480
Thr Ser Pro Glu Gln Ser Thr Asn Val Val Ile Ala Thr Lys Ala Asn
            485                 490                 495
Leu Phe Lys Glu Leu Gly Ile Thr Ser Phe Glu Leu Ala Pro Gln Tyr
        500                 505                 510
Arg Ser Ser Gly Asp Thr Asn Tyr Gly Gly Met Ser Phe Leu Asp Ser
    515                 520                 525
Phe Leu Asn Asn Gly Tyr Ala Phe Thr Asp Arg Tyr Asp Leu Gly Phe
530                 535                 540
Asn Lys Ala Asp Gly Asn Pro Asn Pro Thr Lys Tyr Gly Thr Asp Gln
545                 550                 555                 560
Asp Leu Arg Asn Ala Ile Glu Ala Leu His Lys Asn Gly Met Gln Ala
            565                 570                 575
Ile Ala Asp Trp Val Pro Asp Gln
```

-continued

<210> SEQ ID NO 13
<211> LENGTH: 535
<212> TYPE: PRT
<213> ORGANISM: Lactobacillus reuteri

<400> SEQUENCE: 13

Leu Leu Ala Asn Asp Ile Asp Asn Ser Asn Pro Val Val Gln Ala Glu
 1               5                  10                  15

Gln Leu Asn Trp Leu Tyr Tyr Leu Leu Asn Phe Gly Thr Ile Thr Ala
             20                  25                  30

Asn Asn Asp Gln Ala Asn Phe Asp Ser Val Arg Val Asp Ala Pro Asp
         35                  40                  45

Asn Ile Asp Ala Asp Leu Met Asn Ile Ala Gln Asp Tyr Phe Asn Ala
     50                  55                  60

Ala Tyr Gly Met Asp Ser Asp Ala Val Ser Asn Lys His Ile Asn Ile
 65                  70                  75                  80

Leu Glu Asp Trp Asn His Ala Asp Pro Glu Tyr Phe Asn Lys Ile Gly
                 85                  90                  95

Asn Pro Gln Leu Thr Met Asp Asp Thr Ile Lys Asn Ser Leu Asn His
            100                 105                 110

Gly Leu Ser Asp Ala Thr Asn Arg Trp Gly Leu Asp Ala Ile Val His
        115                 120                 125

Gln Ser Leu Ala Asp Arg Glu Asn Asn Ser Thr Glu Asn Val Val Ile
    130                 135                 140

Pro Asn Tyr Ser Phe Val Arg Ala His Asp Asn Asn Ser Gln Asp Gln
145                 150                 155                 160

Ile Gln Asn Ala Ile Arg Asp Val Thr Gly Lys Asp Tyr His Thr Phe
                165                 170                 175

Thr Phe Glu Asp Glu Gln Lys Gly Ile Asp Ala Tyr Ile Gln Asp Gln
            180                 185                 190

Asn Ser Thr Val Lys Lys Tyr Asn Leu Tyr Asn Ile Pro Ala Ser Tyr
        195                 200                 205

Ala Ile Leu Leu Thr Asn Lys Asp Thr Ile Pro Arg Val Tyr Tyr Gly
    210                 215                 220

Asp Leu Tyr Thr Asp Gly Gly Gln Tyr Met Glu His Gln Thr Arg Tyr
225                 230                 235                 240

Tyr Asp Thr Leu Thr Asn Leu Leu Lys Ser Arg Val Lys Tyr Val Ala
                245                 250                 255

Gly Gly Gln Ser Met Gln Thr Met Ser Val Gly Gly Asn Asn Asn Ile
            260                 265                 270

Leu Thr Ser Val Arg Tyr Gly Lys Gly Ala Met Thr Ala Thr Asp Thr
        275                 280                 285

Gly Thr Asp Glu Thr Arg Thr Gln Gly Ile Gly Val Val Val Ser Asn
    290                 295                 300

Thr Pro Asn Leu Lys Leu Gly Val Asn Asp Lys Val Val Leu His Met
305                 310                 315                 320

Gly Ala Ala His Lys Asn Gln Gln Tyr Arg Ala Ala Val Leu Thr Thr
                325                 330                 335

Thr Asp Gly Val Ile Asn Tyr Thr Ser Asp Gln Gly Ala Pro Val Ala
            340                 345                 350

Met Thr Asp Glu Asn Gly Asp Leu Tyr Leu Ser Ser His Asn Leu Val
        355                 360                 365

```
Val Asn Gly Lys Glu Glu Ala Asp Thr Ala Val Gln Gly Tyr Ala Asn
    370                 375                 380
Pro Asp Val Ser Gly Tyr Leu Ala Val Trp Val Pro Val Gly Ala Ser
385                 390                 395                 400
Asp Asn Gln Asp Ala Arg Thr Ala Pro Ser Thr Glu Lys Asn Ser Gly
                405                 410                 415
Asn Ser Ala Tyr Arg Thr Asn Ala Ala Phe Asp Ser Asn Val Ile Phe
            420                 425                 430
Glu Ala Phe Ser Asn Phe Val Tyr Thr Pro Thr Lys Glu Ser Glu Arg
        435                 440                 445
Ala Asn Val Arg Ile Ala Gln Asn Ala Asp Phe Phe Ala Ser Leu Gly
    450                 455                 460
Phe Thr Ser Phe Glu Met Ala Pro Gln Tyr Asn Ser Ser Lys Asp Arg
465                 470                 475                 480
Thr Phe Leu Asp Ser Thr Ile Asp Asn Gly Tyr Ala Phe Thr Asp Arg
                485                 490                 495
Tyr Asp Leu Gly Met Ser Glu Pro Asn Lys Tyr Gly Thr Asp Glu Asp
            500                 505                 510
Leu Arg Asn Ala Ile Gln Ala Leu His Lys Ala Gly Leu Gln Val Met
        515                 520                 525
Ala Asp Trp Val Pro Asp Gln
    530                 535
```

<210> SEQ ID NO 14
<211> LENGTH: 5
<212> TYPE: PRT
<213> ORGANISM: Neisseria polysaccharea

<400> SEQUENCE: 14

```
Gln Trp Asp Leu Asn
  1               5
```

<210> SEQ ID NO 15
<211> LENGTH: 10
<212> TYPE: PRT
<213> ORGANISM: Neisseria polysaccharea

<400> SEQUENCE: 15

```
Ile Val Arg Met Asp Ala Val Ala Phe Ile
  1               5                  10
```

<210> SEQ ID NO 16
<211> LENGTH: 4
<212> TYPE: PRT
<213> ORGANISM: Neisseria polysaccharea

<400> SEQUENCE: 16

```
Phe Val Arg Ser
  1
```

<210> SEQ ID NO 17
<211> LENGTH: 9
<212> TYPE: PRT
<213> ORGANISM: Neisseria polysaccharea

<400> SEQUENCE: 17

```
Gly Leu Pro Arg Ile Tyr Leu Gly Asp
  1               5
```

<210> SEQ ID NO 18

```
<211> LENGTH: 9
<212> TYPE: PRT
<213> ORGANISM: Neisseria polysaccharea

<400> SEQUENCE: 18

Gly Leu Thr Tyr Leu His Leu Met Pro
 1               5

<210> SEQ ID NO 19
<211> LENGTH: 6
<212> TYPE: PRT
<213> ORGANISM: Neisseria polysaccharea

<400> SEQUENCE: 19

Asp Phe Ile Thr Asn His
 1               5
```

What is claimed is:

1. An isolated protein having glucosyltransferase activity comprising an amino acid sequence, which exhibits at least 95% amino acid homology, as determined by BLAST algorithm, with the amino acid sequence 972–1781 of SEQ ID No. 2.

2. The isolated protein according to claim 1, which exhibits at least 98% amino acid homology with amino acid sequence 972–1514 of SEQ ID No. 2.

3. The protein according to claim 1, wherein said protein comprises amino acids 972–1781 of SEQ ID No. 2.

4. The isolated protein according to claim 1, comprising at least one of the amino acids Pro-1026, Ile-1029, Met-1034, Asn-1035, Ser-1136, Ala-1143, Ile-1168, Leu-1223, Ala-1413, Val-1418, Ala-1428, Leu-1442 in the same relative position as the amino acids of the amino acid sequence of SEQ ID No. 2.

5. The isolated protein according to claim 1 wherein, in the presence of sucrose, produces a glucan having 38–48% 4-linked anhydroglucose units, 17–28% 6-linked anhydroglucose units, and 7–20% 4,6-linked anhydroglucose units.

6. The isolated protein according to claim 1, wherein said protein is a recombinant protein.

7. The isolated protein according to claim 1, which exhibits at least 96% amino acid homology with amino acid sequence 972–1781 of SEQ ID No. 2.

8. The isolated protein according to claim 1, which exhibits at least 97% amino acid homology with amino acid sequence 972–1781 of SEQ ID No. 2.

9. An isolated protein having glucosyltransferase activity comprising an amino acid sequence, which exhibits at least 95% amino acid homology, as determined by BLAST algorithm, with amino acid sequence 531–1781 of SEQ ID No. 2.

10. The isolated protein according to claim 9, comprising an amino acid sequence which exhibits at least 96% amino acid homology with amino acid sequence 531–1781 of SEQ ID No. 2.

11. The isolated protein according to claim 9, comprising an amino acid sequence which exhibits at least 97% amino acid homology with amino acid sequence 531–1781 of SEQ ID No. 2.

12. The isolated protein according to claim 9, comprising at least one of the amino acids Pro-1026, Ile-1029, Met-1034, Asn-1035, Ser-1136, Ala-1143, Ile-1168, Leu-1223, Ala-1413, Val-1418, Ala-1428, Leu-1442 in the same relative position as amino acids of the amino acid sequence of SEQ ID No. 2.

13. The isolated protein according to claim 9 wherein, in the presence of sucrose, produces a glucan having 38–48% 4-linked anhydroglucose units, 17–28% 6-linked anhydroglucose units, and 7–20% 4,6-linked anhydroglucose units.

14. The isolated protein according to claim 9, wherein said protein is a recombinant protein.

15. An isolated protein having glucosyltransferase activity comprising an amino acid sequence 972–1781 of SEQ ID No: 2.

16. An isolated protein comprising an amino acid sequence 531–1781 of SEQ ID No: 2.

17. The isolated protein according to claim 16, wherein in the presence of sucrose, a glucan is produced having 38–48% 4-linked anhydroglucose units, 17–28% 6-linked anhydroglucose units, and 7–20% 4,6- linked anhydroglucose units.

* * * * *